United States Patent [19]

Han et al.

[11] Patent Number: 6,043,276

[45] Date of Patent: Mar. 28, 2000

[54] COMPOUNDS OBTAINED FROM SALVIA SPECIES HAVING ANTIVIRAL ACTIVITY

[75] Inventors: Myun K. Han, Silver Spring; Paul Lee, Phoenix, both of Md.

[73] Assignee: Georgetown University School of Medicine, Washington, D.C.

[21] Appl. No.: 09/339,813

[22] Filed: Jun. 25, 1999

Related U.S. Application Data

[63] Continuation-in-part of application No. 09/104,363, Jun. 25, 1998.

[51] Int. Cl.[7] .......................... A01N 37/10; A61K 31/765
[52] U.S. Cl. ...................... 514/532; 514/533; 424/78.37; 424/195.1
[58] Field of Search ............................. 424/78.37, 195.1; 514/532, 533

[56] References Cited

PUBLICATIONS

Li, "Water Soluble Active Components of Salvia miltiorrhiza and Related Plants", Journal of Chinese Pharmaceutical Sciences 6 (2), pp. 57–64, Jan. 1997.

*Primary Examiner*—Frederick Krass
*Attorney, Agent, or Firm*—Burns, Doane, Swecker & Mathis, LLP

[57] ABSTRACT

Compositions are provided containing molecules having at least one moiety from β-(3,4-dihydroxyphenyl) lactic acid and/or caffeic acid, which are found in extracts from the plant genus Salvia, said moieties being of the formula:

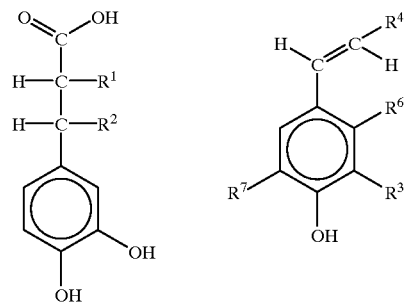

the active agents having a molecular weight of at least 190 daltons. A class of preferred agents are those which are conjugated to form dimers, trimers, tetramers and larger polymers containing said moieties, with the most preferred being salvianolic acid dimers, trimers, tetramers and larger polymers. The compounds and compositions may be administered in pharmaceutically acceptable carriers and excipients systemically or locally to treat viral infections.

39 Claims, 13 Drawing Sheets

COMPOUNDS OBTAINED FROM SALVIA SPECIES HAVING ANTIVIRAL ACTIVITY

CROSS REFERENCE

This application is a continuation-in-part of application No. 09/104,363, filed Jun. 25, 1998.

FIELD OF THE INVENTION

This invention is related to the use of active agents obtained from extracts of the plant genus Salvia. The active ingredients include conjugates of molecules having at least one moiety from β-(3,4-dihydroxyphenyl) lactic acid and/or caffeic acid. The active ingredients are preferably salvianolic acid, its dimers, trimers and tetramers. The active agents, either alone or more preferredly in combination, can be administered to a subject to treat a viral infection or virus mediated condition.

BACKGROUND OF THE INVENTION

*Salvia miltiorrliza*. The plant, *Salvia miltiorrhiza* (SM), has long been used in traditional Chinese medicine for treatment of cardiovascular and hepatic diseases. Extracts from the plant confer potent hepatoprotective activity both in vitro and in vivo. Hase et al., *Planta Med.* 63: 22–6 (1997). Magnesium lithospermate B may be one of the main active components of SM that protects the liver (Liu et al., *Chung Kuo Chung Hsi I Chih Ho Tsa Chih* 13: 352–3, 326 (1993)). SM also contains antioxidants that apparently aid membrane damage repair when treating viral myocarditis (Meng et al., *Chung Kuo Chung Hsi I Chieh Ho Tsa Chih* 12: 345–7, 324–5 (1992)). Patients suffering from chronic hepatitis B have responded to treatment with SM and/or Polyporus Umbellatus polysaccharide (PUP) (Xiong, *Chung Kuo Chung Hsi I Chieh Ho Tsa Chih* 13: 33–5, 516–7 (1993)). Herbal extracts from SM also have demonstrated anti-HIV activity (U.S. Pat. No. 5,178,865) and anti-hepatitis activity (International PCT Application 98/24460; Chinese Patent Application Nos. 1,192,922 and 1,192,918). Antiviral agents active against herpes, polio, measles, varicella zoster, cytomegalovirus, DNA viruses and RNA viruses have been described which contain at least one crude drug from the root of *Salvia miltiorrhiza* Bunge (European Patent No. 568,001). Salvia extracts have also been prepared as anti-herpes virus agents (U.S. Pat. No. 5,411,733).

The SM plant has several components which may be extracted. Components of the root have been extracted initially with ethanol, followed by extraction with cold water (SM(1)) or with hot water (SM(2)). Both fractions extracted in water have shown antiviral activity.

Antiviral agents have been developed which target different points in a virus life cycle. For example, antiviral agents for treating retroviral infections have been developed which target retrovirus specific enzymes such as reverse transcriptase (RT) and integrase. Research continues to identify other antiviral agents to combat diseases such as herpes, hepatitis and influenza.

Antiviral Agents Against Retroviruses. Antiviral agents targeting the integrase protein include peptide inhibitors (U.S. Pat. No. 5,578,573), nucleic acid ligand inhibitors (U.S. Pat. Nos. 5,756,287 and 5,587,468), as well as compounds such as Equisetin (U.S. Pat. Nos. 5,759,842) and ermophilane sesquiterpenoids (U.S. Pat. No. 5,858,738). To date, of the numerous compounds that have already been identified and approved for marketing by the FDA for HIV, only RT and protease inhibitors have been approved.

Caffeic Acid as an Antiviral Agent. Caffeic acid can be isolated from the stems of *Bougainvillea spectabillis* Wild (Nyctaginaceae), which has been used as folk medicine against hepatitis (Chang et al., *Anticancer Res.* 14: 501–6 (1994)). Caffeic acid has been reported to inhibit xanthine oxidase, which is associated with several diseases, e.g., gout, hepatitis and tumors (Chan et al., *Anticancer Res.* 15: 703–7(1995); and Chang et al. (1994)). Caffeic acid oxidation product (KOP) inhibits herpes virus hominis type 1 and type 2 (Thiel et al., *Acta Virol.* 27: 200–8 (1983)). A caffeic acid tetramer and dipotassium and potassium-sodium salts of a caffeic acid tetramer glucoside possess anti-HIV activity according to Kashiwada et al., *J. Nat. Prod.* 58: 392–400 (1995). Commercially produced caffeic acid also has antiviral activity, as demonstrated using a RT assay for HIV (Kreis et al., *Antiviral Res.* 14: 323–37 (1990)). Caffeic acid phenethyl esters (CAPE) exert inhibitory activity on the integrase protein of HIV- 1 (Fesen et al., *Proc. Natl Acad. Sci. USA* 90: 2399–2403 (1993); Fesen et al., *Biochem. Pharmacol.* 48: 595–608 (1994); Burke et al.,*J. Med. Chem.* 38: 4171–8 (1995); Mazumder et al., *J. Med. Chem.* 39: 2472–81 (1996)). However, the method used to prepare caffeic acid polymers influenced their HIV-1 and HIV-2 inhibitory activity (Nakashima et al., *Chem. Pharm. Bull.* (Tokyo) 40: 2102–5 (1992)). Caffeic acid, along with cinnamic acid and rosemarinic acid, have also been proposed for treating influenza virus because of their antioxidant activity (International PCT Application 98/30228).

Rosemarinic and Lithospermic Acids as Antiviral Agents. Rosemarinic acid is a dimer of caffeic acid. A dimer of rosemarinic acid is lithospermate B. Both rosemarinic acid and lithospermic acid have been identified in extracts of SM root (Kohda et al., *Chem. Pharm. Bull.* (Tokyo) 37: 1287–90 (1989)). Rosemarinic acid possesses anti-HIV activity (Arda et al., *J. Nat. Prod.* 60: 1170–3 (1997)) and is potentially a Herpes simplex type 1 (HSV-1) inhibitor (Dimitrova et al., *Acta Microbiol. Bulg.* 29: 65–72 (1993)). Rosemarinic acid also has been proposed to treat inflammatory diseases and disorders (U.S. Pat. No. 4,329,361).

Cinnamic Acid as an Antiviral Agent. Substituted cinnamic acid esters inhibit the infectious activity of influenza virus A/Hong Kong (H3N2) (Serkedjieva et al.,*J. Nat. Prod.* 55: 294–302 (1992)); steryl esters of cinnamic acid derivatives have demonstrated antiviral activity in vitro against viruses belonging to *Picornaviridae, Orthomyxoviridae, Paramyxoviridae* and *Herpesviridae* ("Antiviral activity of cholesteryl esters of cinnamic acid derivatives," Z. Naturforsch 53: 883–7 (1998); and Conti et al., *Antivir. Chem. Chemother.* 9: 511–5 (1998)). Dehydrogenation polymers of substituted cinnamic acids have also been described as a HIV-1 therapeutic (U.S. Pat. Nos. 5,346,695 and 5,632,980).

Salvianolic Acid. Salvianolic acid has not been described in the literature as having antiviral properties. Several forms of salvianolic acid (e.g., salvianolic acid A, acetylsalvianolic acid ) have been described as having antioxidant properties (Lin et al., *J Biochem. Pharmacol.* 51: 1237–1241 (1996). Salvianolic acid has also been indicated for preventing liver injury and fibrosis, associated with its anti-lipid peroxidation actions (Hu et al.,*Acta Pharmacol. Sin.* 18: 478–480 (1997)) and for use in treating coronary diseases (Japanese Patent 2,131,423). Additional forms of salvianolic acid described in the literature include those isolated from aqueous extracts of *Salvia cavaleriei* (e.g., salvianolic acids A, B, C H and I) (Zhang et al., *Planta Med.* 60: 70–72 (1994)) or from *S. miltiorrhiza* (e.g., salvianolic acid K, a caffeic acid trimer) (Kasimu et al., *Chem. Pharm. Bull.* 46: 500–504 (1998); and Tezuka et al., *Chem Pharm. Bull.* 46: 107–112 (1998)).

Salvianolic acids F 2 and F 3 can be prepared synthetically as described by Dalla et al., *Tetrahedron* 55: 6923–6930 (1999); and Dalla et al., *Tetrahedron Lett.* 39: 8285–8286 (1998). Additional members of the Salvia family may be used as sources for obtaining Danshen, including: *S. bowleyana, S. deserta, S. miltiorhiza* var. miltiorhiza f. alba, *S. paramiltiorhiza, S. paramiltiorhiza* f. purpureo-rubra, *S. przewalskii, S. prsewalskii* var. mandarinorum, *S. sinica* f. purpurea, and *S. trijuga*) (Kasiumu et al., 1998). Methods of producing plants with elevated secondary metabolite levels of compounds such as salvianolic acid have also been described. See U.S. Pat. No. 5,869,340 (1999).

(3,4-dihydroxyphenyl) lactic acid. A principle component of SM is "Danshensu," chemically known as sodium δ-3, 4-dihydroxyphenyl lactate (Fen et al., *Acta Acad. Med. Primae Shanghai* 10: 133–6 (1983); Zhao et al., *Chin. Pharm. J.* 29: 291–93 (1994)). It is an intermediate compound used in preparing rosemarinic acid in cell culture (Al-Sereiti et al., *Indian J Exp. Biol.* 37: 124–130 (1999); Bogucki et al., *Can. J Chem.* 75: 1783–94 (1997); and U.S. Pat. No. 5,011,775).

Treating virus-mediated diseases with antiviral agents can be quite expensive. For example, HIV-1 treatment using reverse transcriptase and protease inhibitors costs approximately $12,000–20,000 per patient per year. Given that the majority of HIV infected patients reside in developing nations, additional medications which are more economically attractive must be identified for the treatment of HIV and other viral diseases. The instant invention provides a new method of identifying, making and using novel compounds and compositions thereof for use as antiviral therapeutics.

SUMMARY OF THE INVENTION

One aspect of the invention describes compositions containing molecules having at least one moiety from β-(3,4-dihydroxyphenyl) lactic acid and/or caffeic acid, which are found in extracts from genus Salvia, said moieties being of the formula:

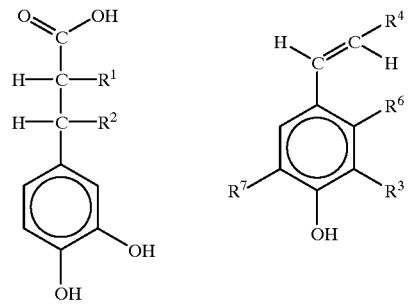

said active agents having a molecular weight of at least 190 daltons. $R^1$ of the β-(3,4-dihydroxyphenyl) lactic acid moiety can be either —OH, —O— or a bond, and $R^2$ can be either —H or a bond. $R^3$ of the caffeic acid moiety can be either —OH or —O—; $R^4$ can be either a bond or

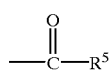

wherein $R^5$ is —OH or a bond; $R^6$ can be either —H or a bond; and $R^7$ can be either —H or a bond.

In another embodiment, a conjugation product is contemplated, which is a homopolymer or heteropolymer of monomeric units of salvianolic acid and/or dehydrogenated forms of salvianolic acid, said conjugation product having a molecular weight of about 492 or greater, or acetyl, ester, or anhydride derivatives thereof, or pharmaceutically acceptable salts thereof. In a preferred embodiment, the conjugation product is a homopolymer or heteropolymer of monomeric units of salvianolic acid (I) and/or dehydrogenated forms (II) or (III) of salvianolic acid, said salvianolic acid having the structure:

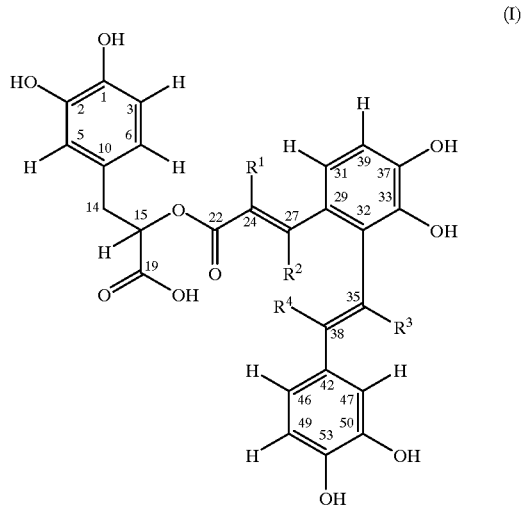

and said dehydrogenated forms of salvianolic acid having the structures:

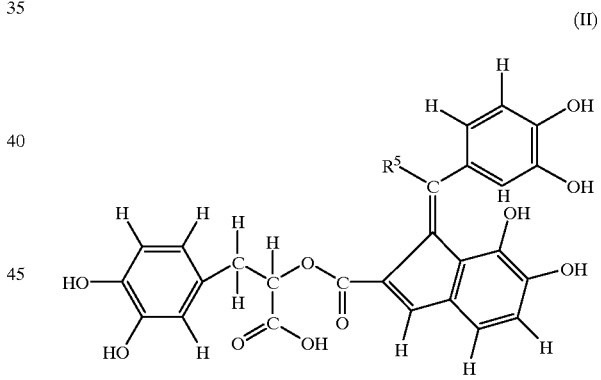

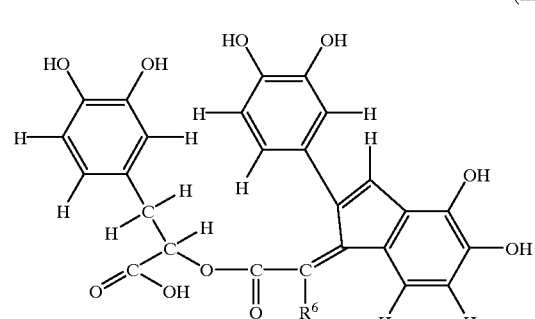

wherein $R^1$, $R^2$, $R^3$, $R^4$, $R^5$, and $R^6$ are hydrogen or a bond, and the monomeric units of said homopolymers or heteropolymers are bonded to each other by $R^1$, $R^2$, $R^3$, $R^4$, $R^5$, and $R^6$.

The present invention also relates to a method of making an antiviral agent comprising incubating salvianolic acid at an alkaline pH such that homopolynmers or heteropolymers are formed which possess greater antiviral activity than salvianolic acid.

The agents of the invention possess antiviral activity and may be administered in pharmaceutically acceptable carriers systemically or locally.

DETAILED DESCRIPTION OF THE INVENTION

Figure 1:
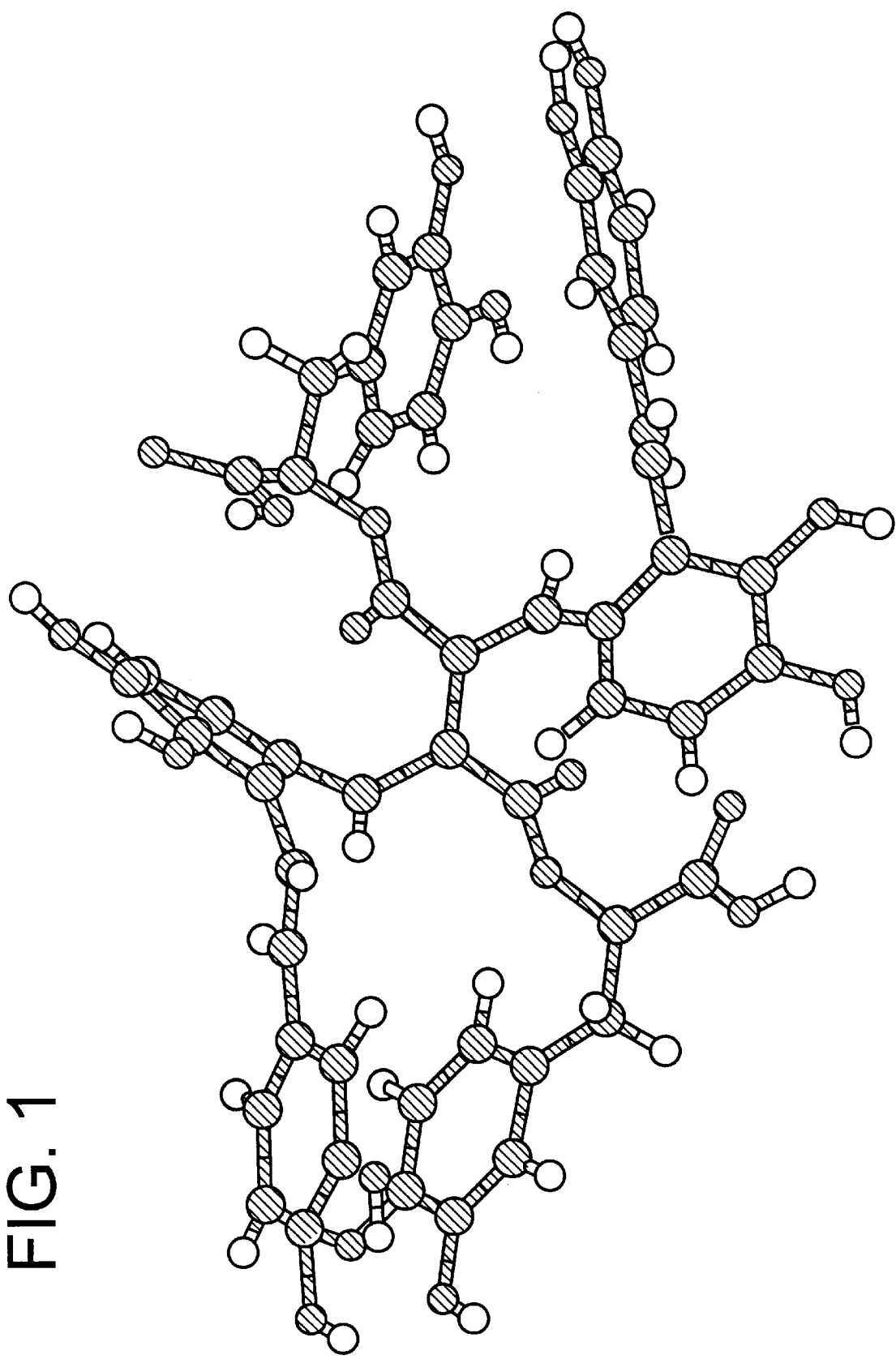
FIG. 1. Three-dimensional representation of Compound 5 of Example 4.

This invention uses an alternative approach to develop drugs derived from plant extracts, specifically the extracts from the plant genus Salvia. These active agents inhibit viral integration in a variety of different viruses, including retroviruses. In one preferred embodiment, the active agents disclosed inhibit integration of all or a portion of a viral genome into the genome of the host cell. The active agents also may inhibit virus infection, virus progression and/or virus proliferation by interfering at other points in a virus life cycle.

The Salvia genus (family Lamiaceae) contains about 700 members that are located in the tropical and temperate zones of the world, with some 300 species in Asia, Europe and Africa and 400 species in America (J.C. Willis, A DICTIONARY OF FLOWERING PLANTS AND FERNS (7th edition, Cambridge, University Press, 1966); J. Briquet, Labiatae, In DIE NATURLICHEN PFLANZENFAMILIEN Vol. IV, 3a, 183–375 (Engler and Prantl eds., Englemann, Leipzig, 1897). The antiviral compounds and compositions of this invention may be derived from any member of the Salvia genus, but preferably from SM and SY.

A. DEFINITIONS

By the terms "viral-inhibiting effective amount," "therapeutically effective amount" or "therapeutically effective dose" is meant that amount of an active agent or active agents that when administered to a subject with a viral infection or virus mediated disease, said infection or disease is ameliorated, or infection inhibited to an extent that outweighs any negative side effects caused by the agent or agents. Such agents would be considered "antiviral agents."

By "viral mediated condition" or "virus mediated condition" is meant a disease phenotype associated with a viral infection. For example, AIDS-related complex (ARC) is a condition associated with an HIV-1 infection.

By "antiviral activity" is meant an ability to inhibit or ameliorate a viral infection or a condition associated with a viral infection. Compounds having antiviral activity according to the invention will preferably inhibit infection in vitro at a dosage of $\leq 1$ $\mu$M, or less preferably less than or equal to about 10 mM in vitro.

By "integrase activity" is meant an integrase protein or a protein which can integrate a viral genome or segment of a viral genome into the genome of a host cell. The majority of integrase proteins are associated with members of the Retroviridae family of viruses.

By "plant genus Salvia" is meant a plant from the genus Salvia, the family Lamiaceae. Preferred Salvia plants for isolation of compounds according to the invention are "Salvia miltiorrhiza" or "SM" and "Salvia yunanesis" or "SY."

By "conjugated derivatives" or "larger polymers" is meant an active agent which comprises a dimer, trimer, tetramer, etc. wherein the monomeric unit is one of the following moieties:

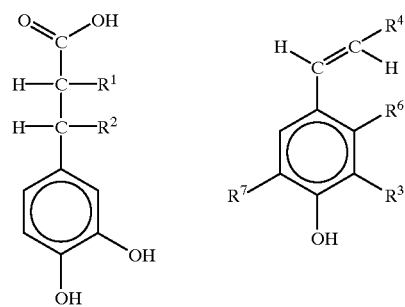

The conjugated derivatives or large polymers may be homodimers, homotrimers, homotetramers, etc., or heterodimers, heterotrimers, heterotetramers, etc., of the foregoing moieties. One example of a conjugate derivative is lithospermate B which is a dimer of rosemarinic acid which in turn is a dimer of caffeic acid.

B. VIRUSES

Treatment or inhibition of any viral infection responsive to the antiviral compounds and compositions described herein is within the scope of the present invention. Preferred are viruses of the following virus families: hepatitis viruses, herpes viruses, orthomyxoviruses, papillomaviruses, paramyxoviruses, picomaviruses, polyomaviruses and retroviruses.

Retroviruses. The compounds and compositions described herein preferredly will be used to treat retroviral infections. Although retroviruses belong to a clearly defined and relatively homogeneous viral genus, they have been historically subdivided into three taxonomic groupings, primarily on the basis of the pathologic consequences of infection. The oncovirus subgroup includes retroviruses that have the ability to cause neoplastic disease in the infected host, as well as several related, yet apparently benign viruses. Lentiviruses cause slow, chronic diseases that generally, although not always, lack a neoplastic component. Lentiviruses have yet to be clearly associated with any human or animal disease.

Retroviral replication initiates with the intracytoplasmic penetration of the virion core, a process mediated by the specific interaction of the viral envelope glycoprotein with a specific cell surface receptor. Subsequently, a virion-associated RNA-dependent DNA polymerase transcribes the single-stranded RNA genome into a double-stranded linear DNA proviral intermediate (reverse transcription). An integration protein (integrase) specifically recognizes both ends of the viral DNA and removes two nucleotides from the 3'-ends (3'-donor processing). The processed viral DNA and integrase then migrate to the nucleus, where a viral integrase covalently links the retroviral genome to host chromosomal DNA (strand transfer), thereby forming the retroviral provirus.

The emergence of human immunodeficiency virus type 1 (HIV-1) as an important human pathogen increased scientific interest in retroviruses. In particular, evidence indicates that the simple life cycle delineated above is not completely descriptive of the replication cycle of all the retroviruses. For example, HIV-1 encodes no fewer than six gene products in addition to the characteristic retroviral Gag, Pol, and Env; these are translated from a novel set of singly spliced and multiply spliced viral mRNA species. At least two of these additional proteins, termed Tat and Rev, act in trans to directly regulate HIV-1 gene expression. Therefore, the steps between penetration and proviral integration appeared quite similar for both MLV (murine leukemia virus) and HIV-1, although postintegration events were found to be significantly more complex in the latter. More recently, it has become evident that HIV-1 is merely one of a whole class of animal retroviruses, that are now referred to as "complex" retroviruses. Retroviruses belonging to this complex retroviruses include all lentiviruses, spumaviruses, as well as HTLV-1 and related viruses (Table 1).

TABLE 1

| Category | Major taxonomic divisions among retroviruses Subgroup | Prototype | Other examples |
|---|---|---|---|
| Simple retroviruses | C-type retroviruses group A | RSV | ALV, ASV |
|  | C-type retroviruses group B | MLV | FeLV, MSV, SNV, REV, SSV |
|  | B-type retroviruses | MMTV |  |
|  | D-type retroviruses | MPMV | SRV-1 |
| Complex retroviruses | Lentiviruses | HIV-1 | HIV-2, SIV, visna virus, FIV, |
|  | T-cell leukemia viruses Spuma- | HTLV-1 | EIAV HTLV-II, STLV, BLV |
|  | viruses | HSRV | SFV, BFV |

Abbreviations: RSV, Rous sarcoma virus; ALV, avian leukemia virus; ASV, avian sarcoma virus; FeLV, feline leukemia virus; MSV, murine sarcoma virus; SNV, spleen necrosis virus; REV, reticuloendotheliosis virus; SSV, simian sarcoma virus; MMTV, mouse mammary tumor virus; MPMV, Mason-Pfizer monkey virus; SRV-1, simian retrovirus type 1; STLV, simian T-cell leukemia virus; BFV, bovine foamy virus.

The steps involved in proviral integration appear quite similar for both simple and complex retroviruses. Because of this commonality of mechanism, an inhibitor of retroviral integrase will inhibit a wide range of organisms such as human immunodeficiency virus (HIV), simian immunodeficiency virus (SIV), Feline Immunodeficiency Virus (FIV), Feline Leukemia Virus (FeLV), Murine leukemia virus (MuLV), Rous Sarcoma Virus (RSV), Bovine Immunodeficiency Virus (BIV), Human T-Cell Leukemia virus (HTLV). In addition to these retroviruses, the active agents of the invention may be used as inhibitors against integrase-like proteins to inhibit replication other viruses, such as the Hepatitis B virus (HBV).

Other Viruses. The active agents described herein are also contemplated for use in treating viral infections caused by, for example, hepatitis viruses, herpes viruses, orthomyxoviruses, papillomaviruses, paramyxoviruses, picornaviruses and polyomaviruses. Preferred viruses to be treated with the active agents described herein include those listed in the table below:

TABLE 2

| Virus Family | Common Name | Host Animal |
| --- | --- | --- |
| Hepadnavindae | Hepatitis B | Human |
| | Woodchuck hepatitis virus | Woodchuck |
| | Duck hepatitis B virus | Avian |
| Herpesviridae | Herpes simplex virus 1 | Human |
| | Herpes simplex virus 2 | Human |
| | Varicella zoster virus | Human |
| | Epstein Barr virus | Human |
| | Cytomegalovirus | Human |
| | Infectious bovine Rhinotracheitis virus | Mammal |
| | Bovine mammillitis virus | Mammal |
| | Equine abortion virus | Mammal |
| | Pseudorabies virus | Mammal |
| | Marek's disease | Avian |
| | Turkey herpesvirus | Avian |
| Orthomyxovirinae | Influenza Type A | Many species |
| | Influenza Type B | Mainly Human |
| | Influenza Type C | Mainly Human |
| Papillomavirinae | Bovine Papilloma Virus-1 (BPV-1) | Cattle |
| | Bovine Papilloma Virus-2 (BPV-2) | Cattle |
| | Bovine Papilloma Virus-4 (BPV-4) | Cattle |
| | CRPV | Rabbit |
| | DPV | Deer |
| | Human Papilloma Virus-1 (HPV-1) | Human |
| | HPV-5 | Human |
| | HPV-6 | Human |
| | HPV-8 | Human |
| | HPV-11 | Human |
| | HPV-16 | Human |
| | HPV-18 | Human |
| | HPV-31 | Human |
| | HPV-33 | Human |
| Paramyxovirinae | Human parainfluenza viruses types 1–4 | Human |
| | SV5 | Dog |
| | Mumps Virus | Human |
| | Newcastle disease virus | Chicken |
| | Measles virus | Human |
| | Canine distemper virus | Dog |
| | Rinderpest virus | Catte |
| | Respiratory syncytial virus (RSV) | Human |
| | Bovine respiratory syncytial virus | Cattle |
| Picornavirinae | Human polio virus | Human |
| | Human coxsackievirus | Human |
| | Human echovirus | Human |
| | Human enterovirus | Human |
| | Human hepatitis virus A | Human |
| | Porcine enteroviruses 1–11 | Pig |
| | Bovine Enteroviruses 1 and 2 | Cattle |
| | Human Rhinovirus 1–100 | Human |
| | Bovine rhinoviruses 1 and 2 | Cattle |
| | Foot-and-mouth disease viruses 1–7 | Cattle and Human |
| | Encephalomyocarditis Equine rhinoviruses 1 and 2 | Horse |
| Polyomavirinae | Polyomavirus | Mouse |
| | Simian vacuolating virus 40 (SV40) | Monkey |
| | Lymphotropic papovavirus (LPV) | Monkey |
| | BKV | Human |
| | JCV | Human |
| | Rabbit kidney vacuolating virus (RKV) | Rabbit |

See FUNDAMENTAL VIROLOOY (Bernard N. Fields et al., eds., 1991).

C. METHODS OF MAKING THE COMPOUNDS

The general conditions for preparing the plant extracts from any Salvia species, and more preferred from SM and SY, which contain the active agents is as described in Example 1 below. The compounds can be prepared synthetically as follows. Various compounds containing the moieties β-(3,4-dihydroxyphenyl) lactic acid or salvianolic acid and/or caffeic acid were formed by incubation of the respective compounds at a concentration of 5 mg/ml in 0.1% $NH_4OH$ for up to 24 hrs. These include the dehydrogenated forms of salvianolic acid, conjugated dimers and larger polymers. The preferred period of time is 3–24 hrs. Incubation periods greater than 48 hrs. in 0.1% $NH_4OH$ may result in inactivation of the compound. The period of activation also depends on the starting concentration of the compound. Higher concentrations of compound will require longer periods of incubation for activation. This formation can also occur by adjusting the pH of the compounds in solution to greater than pH=8 by other alkaline reagents. The reaction is stopped by the addition of an acid, such as 1% acetic acid, such that the pH of the resulting solution is less than or equal to 7. Other factors that can contribute to the formation of new compounds are temperature and oxygenation.

D. PHARMACEUTICAL COMPOSITIONS AND THEIR ADMINISTRATION

For the treatment or mediation of viral infections, a compound according to the invention may be administered orally, topically, parenterally, by inhalation spray or rectally, in dosage unit formulations containing conventional non-toxic pharmaceutically acceptable carriers, adjuvants and vehicles. The term "parenteral," as used herein, includes subcutaneous injections, intravenous, intramuscular, intravascular injection or infusion techniques. In addition to the treatment of warm-blooded animals such as mice, rats, horses, cattle, sheep, dogs, cats, etc., the compounds and compositions described herein are effective in the treatment of virus infections in human subjects.

For administration to the central nervous system, compositions may be administered into the cerebral spinal fluid. For intrathecal administration, carriers for parenteral administration, particularly carriers such as glucose in water or saline, are appropriate. The compositions may also be prepared in liposomes to enhance transfer across membrane barriers. Compositions may be prepared for transdermal administration via patches. Solvents used for administration of hydrophobic compounds may also be used for this purpose, such as DMSO or oils which cross the dermal barrier.

For parenteral administration, solutions of a therapeutic compound of the present invention may be prepared, for example, using either sesame or peanut oil or aqueous propylene glycol. Aqueous solutions should be suitably buffered (preferably pH greater than 8) if necessary, and the liquid diluent first rendered isotonic. Such aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known for the manufacture of pharmaceutical compositions, and such compositions may contain one or more agents selected from the group consisting of sweetening agents, flavoring agents, coloring agents and preserving agents in order to provide pharmaceutically palatable preparations. Tablets may contain the active ingredient in admixture with non-toxic pharmaceutically acceptable excipients, which are suitable for the manufacture of tablets.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound or combination of compounds may be combined with various sweetening or flavoring agents, coloring matter or dyes, and, if so desired, emulsifying and/or suspending agents as well, together with such diluents as water, ethanol, propylene glycol, glycerin and various like combinations thereof Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

The excipients may be for example, inert diluents, such as calcium carbonate, sodium carbonate, lactose, calcium phosphate, sodium phosphate; granulating and disintegrating agents, for example, corn starch, or alginic acid; binding agents, for example, starch, gelation or acacia; and lubricating agents, for example magnesium stearate, stearic acid or talc. The tablets may be uncoated, or they may be coated by known techniques to delay disintegration and absorption in the gastrointestinal tract and thereby provide a sustained action over a longer period. For example, a time delay material such as glyceryl monostearate or glyceryl disterate may be employed. They may also be coated by the techniques described in U.S. Pat. Nos. 4,256,108; 4,166,452; and 4,265,874 to form osmotic therapeutic tablets for controlled or timed release.

Aqueous suspensions may contain the active materials in admixture with excipients suitable for the manufacture of aqueous suspensions. Such excipients include suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadccaethyleneoxycetanol, or condensation products of ethylene oxide with partial esters derived from fatty acids and a hexitol such as polyoxyethylene sorbitol monooleate, or condensation products of ethylene oxide with partial ester derived from fatty acids and hexitol anhydrides, for example, polyoxyethylene sorbitan monooleate. The said aqueous suspensions may also contain one or more preservatives, for example, ethyl, or n-propyl p-hydroxybenzoate.

An oily suspension may be formulated by suspending the active ingredient in a vegetable oil, for example, arachis oil, olive oil, sesame oil or coconut oil, or in a mineral oil, such as liquid paraffin. The oily suspensions may contain a thickening agent, for example, beeswax, hard paraffin or cetyl alcohol. These compositions may be preserved by the addition of an antioxidant, such as ascorbic acid.

Dispersible powders and granules are suitable for the preparation of an aqueous suspension by mixing them with water. These compositions may provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally-occurring phosphatides, for example, soy bean, lecithin, and esters or partial ester derived from fatty acids and hexitol anhydrides (e.g., sorbitan monooleate), and condensation products of the said partial esters with ethylene oxide (e.g., polyoxyethylene sorbitan monooleate).

An ointment containing the pharmaceutical compositions of the present invention may be prepared, among other methods known in the art, by combining the active ingredient with a medium consisting of a glycol, a lower alkanol, and water; a gelling agent and optionally an adjuvant such as diisopropyl adipate, diethyl sevacate, ethyl carproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose (e.g., hydroxyethyl cellulose, methyl cellulose, carboxymethyl cellulose, hydroxypropyl cellulose) is used as the gelling agent.

The compounds and compositions described herein may also be administered in the form of suppositories for rectal administration of the drug. These compositions can be prepared by mixing the drug with a suitable non-irritating excipient, which is solid at ordinary temperatures such as room temperature but liquid at the rectal temperature and will therefore melt in the rectum to release the drug. Such materials are cocoa butter and polyethylene glycols.

The amount of an active compound or combination of compounds that may be combined with the carrier materials to produce a single dosage will vary depending upon the host treated and the particular mode of administration. Dosage unit forms will generally contain from about 25 mg to about 1 g of active ingredient. Daily dose of the active ingredients will usually range from between about 1 to about 300 mg per kg of body weight for the oral route and from between about 0.1 to 100 mg per kg of body weight for usual injection administration. The quantity may be given at one time or divided into two or more aliquots administered during the course of a day. It will be understood, however, that the specific dose level for any particular patient or subject will depend upon a variety of factors including the activity of the specific compound employed, the age, body weight, general health, sex, diet, time of administration, route of administration, rate of excretion, drug combination, the duration of viral infection in the subject being treated, and the severity of the particular viral infection being treated.

The compounds of the invention may be administered alone or in combination with pharmaceutically acceptable carriers or diluents by any effective route, preferably by one of the three routes previously indicated. Such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like, as described above.

The examples provided below serve merely to illustrate certain embodiments of the claimed invention and are not meant to limit the invention.

EXAMPLE 1

Extraction of Antiviral Agents from SM and SY

Plant extracts of SM and SY were prepared as follows:

Step 1: Dried SY was boiled in Milli-Q distilled water (dH$_2$O) (18.0 mOhm/cm) and concentrated to a final density of 1.30 g/ml. The extract was then diluted 1:5 with dH$_2$O, centrifuged at 8,000 rpm for 90 min at 25° C. in a GS-3 rotor. The pellet was discarded, and the supernatant was saved. To this supernatant a one tenth volume of 1.0 N HCl solution was added to make a final concentration of 0.1 N HCl. This supernatant was incubated overnight at 25° C. The solution was centrifuged at 8,000 rpm for 90 min at 25° C. in a GS-3 rotor, and the resulting pellet was then washed with 95% ethanol followed by filtration through a 0.2 μm filter system. This was repeated until the wash solutions became clear. The pellet was then dried in the filtration unit at room temperature followed by incubation in an oven overnight at 70° C. The powder was resuspended in dH$_2$O at a 1:5 (w/w) ratio of pellet to water. The resulting product was then centrifuged at 25,000 rpm for 30 min at 25° C. in a Ti45 rotor. The supernatant was discarded, and the resulting pellet resuspended in 50% ethanol. Alternatively, the supernatant can also be resuspended in 50% methanol.

Step 2: The resuspended solution was filtered to remove the insoluble materials.

Step 3: The filtered solution was concentrated to one-fifth (⅕) of the original volume to form a precipitate. The precipitated pellet was washed with distilled water. The washed pellet was then freeze-dried overnight. The dried, washed pellet was designated as Fraction 1.

Step 4: The dried powder obtained from step 3 was dissolved in 50% methanol. The solution was centrifuged to remove any insoluble materials. The supernatant solution was applied to a Sephadex LH-20 column equilibrated with distilled water. The column was washed extensively with distilled water and was eluted with the following order of solutions: 15% methanol in water (v/v), 30% methanol with 1% acetic acid in water (v/v), 40% methanol in water (v/v), 50% methanol in water (v/v), 75% methanol in water (v/v), and 100% methanol. The order of solution used depends on the starting solution. The fraction eluted with 50% methanol in water was concentrated and applied to an HPLC reverse column (Ultrasphere ODS, 4.6×250 mm, 5 μM), which was equilibrated with 10% methanol and 0.1% formic acid. The column was eluted using a 25 minute gradient of 10% methanol/0.1% formic acid and 100% methanol/0.1% formic acid at 1 ml/min. Compounds were detected by monitoring the absorbance at 275 nm.

Step 5: Molecular mass of each fraction eluted from the HPLC reverse column was analyzed by mass spectroscopic methods. The mass spec. identified the following compounds:

| | MW | Compounds |
|---|---|---|
| 1. | 180 | Caffeic acid (#1) |
| 2. | 198 | D-(3,4-dihydroxyphenyl) lactic acid (#2) |
| 3. | 359 | Rosemarinic acid (#3) |
| 4. | 387 | Salt forms of rosemarinic acid (Yunnaneic acid C and Yunnaneic acid D) |
| 5. | 494 | 2-(3,4-dihydroxyphenylethenyl) caffeic acid (#5) or salvianolic acid. |
| 7. | 717 | Lithospermate B (#7) |
| 8. | 739 | Magnesium lithospermate B (#8) |
| 9. | 853 | Combination of rosemarinic acid and 2-(3,4-dihydroxyphenylethenyl) caffeic acid (#9) |
| 10. | 987 | Dimers of #5 with a MW of 987 (#10), as discussed in Example 4, below. |

Compounds are of the formulae:

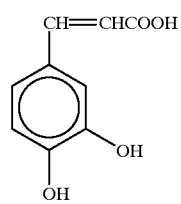

1

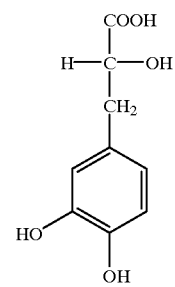

2

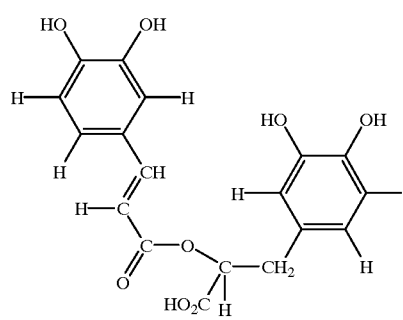

3

Yunnaneic Acid C
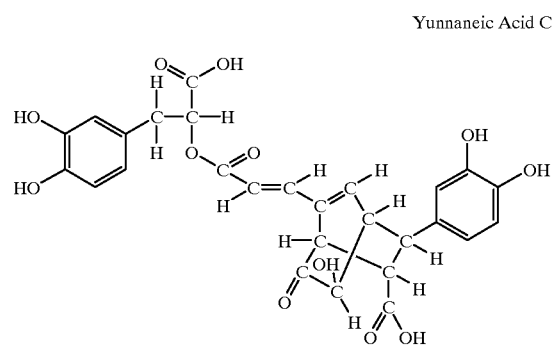
Yunnaneic Acid D
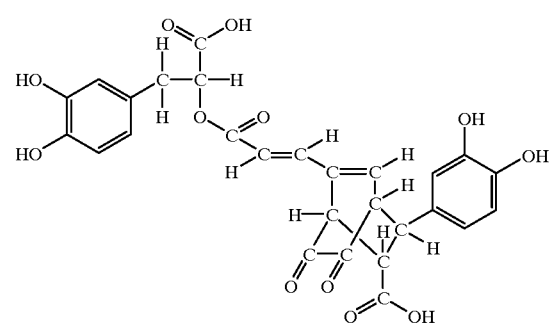
5
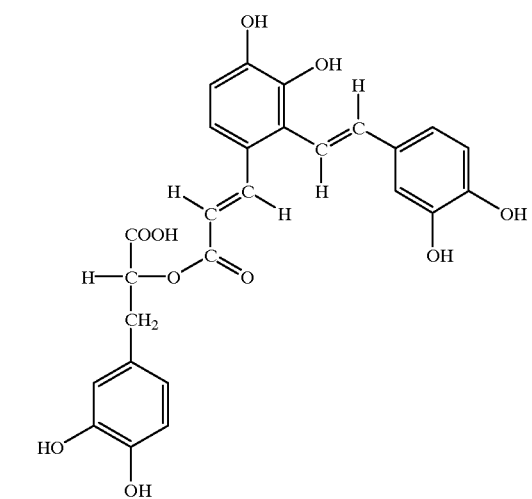
7
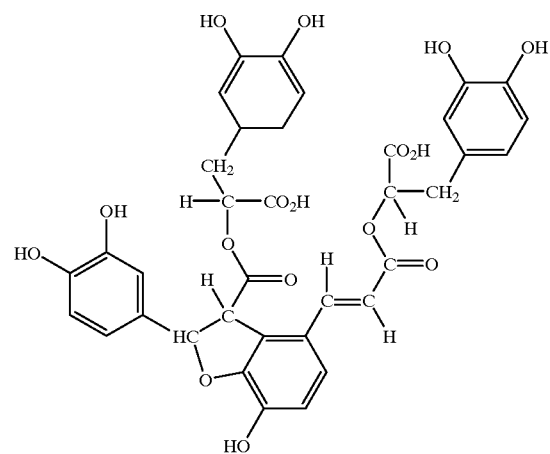
8
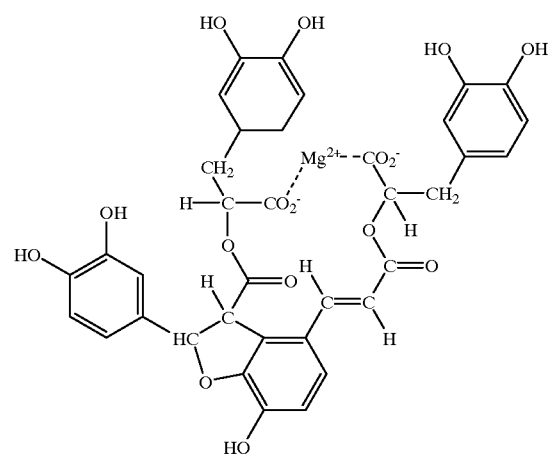
9
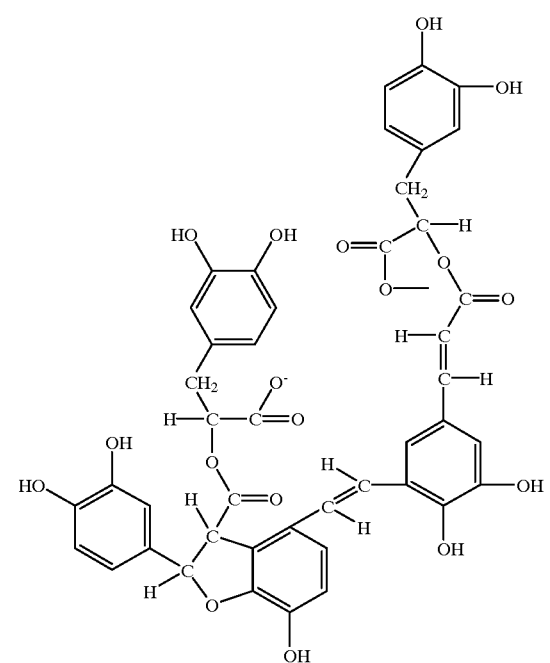

EXAMPLE 2

Antiviral Assay: Efficacy of Viral Inhibition

In vitro HIV-1 Integrase Assay: In vitro assays to monitor the activity of HIV-1 integrase have been developed, as described below. These assays utilize purified recombinant HIV-1 integrase and oligonucleotide substrates which represent the LTR ends of the viral DNA. The functional significance of data obtained from the in vitro assays relies on the assays reflecting the actual functional events which occur in vivo. Both fluorometric (Lee et al., *Analytical Biochemistry* 227: 295–301 (1995)) and radioactive assays have been developed which improve upon the previously published in vitro assay (Lee et al., *Biochemistry* 34: 10205–10214 (1995); Lee et al., *Biochemistry* 34: 10215–10223 (1995)). In addition, we have modified the enzyme preparation, which has improved the quality of the HIV-1 integrase sample (Lee and Han, *Biochemistry* 35: 3837–3844 (1996); Lee et al., *Biochemistry* 36: 173–180 (1997)). These modifications to the in vitro assay and sample preparation have been included to better reflect the events occurring in vivo. Therefore, the results from the in vitro assay are very useful predictors of viral infectivity when searching for potential integrase inhibitors.

The activity of Fraction 1 in inhibiting HIV-1 integrase was determined as follows. Fraction 1 was first dissolved in the appropriate volume of 0.1% $NH_4OH$ (w/v) to make the final concentration 15 mg/ml. These samples were then centrifuged at 10,000 rpm for 30 min. If a pellet was formed, then the supernatant was removed; the pellet was dried down and then redissolved in 0.1% $NH_4OH$. The resulting solution is the stock solution of the extract fractions. From this stock, the following dilutions were made: 1:10, 1:50, 1:100, 1:200, 1:300, 1:400, 1:500, 1:600, 1:700, 1:800, 1:900, 1:1000, 1:2000, 1:3000, 1:4000, 1:5000, and 1:10,000. 1 $\mu$l of each of these dilutions was added to each reaction mixture which corresponds to a final concentration of 75, 15, 7.5, 3.75, 2.5, 1.875, 1.5, 1.25, 1.07, 0.9375, 0.833, 0.75, 0.375, 0.25 0.1875, 0.15 and 0.075 $\mu$g/ml, respectively. Testing was then carried out as previously described (Lee et al., *Biochemistry* 34: 10205–10214 (1995); Lee et al., *Biochemistry* 34: 10215–10223 (1995); Lee and Han (1996)).

To determine the $IC_{50}$ and $IC_{90}$ of each fraction, the gel was exposed to a PHOSPHORIMAGER™ screen and the percent cleavage determined by the Molecular Dynamics PHOSPHORIMAGER™. The percent inhibition was determined by subtracting percent cleavage of each fraction from the percent cleavage of the positive control and dividing this value by the percent cleavage of the positive control. The results demonstrated that Fraction 1 had an $IC_{50}$ of 0.2–1.2 $\mu$g/ml and an $IC_{90}$ of 2.5–3.5 $\mu$g/ml in the culture media. Accordingly, in the live mammal, blood concentrations of up to about 100× that level may be tolerated and beneficial.

EXAMPLE 3

Testing SM Extracts in Vitro

The Feline Immunodeficiency Virus (FIV) model is an accepted animal model for studying drugs for use against HIV infection. FIV is a T cell-trophic lentivirus isolated from felines. FIV resembles HIV biologically and biochemically, which includes high homology between FIV and HIV integrase. FIV infected cats develop Feline Acquired Immunodeficiency Syndrome (FAIDS), which is similar to full-blown AIDS in humans.

In vitro FIV model in cell culture: The Crandell-Reese Feline kidney (CrFK) cell line is susceptible to FIV infection and supports viral replication. CrFK cells are an efficient means for producing virus and assaying for FIV infection. Although FIV is not cytopathic for FIV infected CrFK cells, diagnostic assays are available for screening for FIV infection in tissue culture. Studies have demonstrated the efficacy of SY.

Determination of $ED_{50}$: Fraction 1 was tested for protection of CrFK cells from FIV infection. In triplicate, CrFK cells were plated at a density of $1\times10^5$ cells/T25 flask. Following a 24 hr incubation for cell attachment and growth, solutions of compounds were applied to the cell cultures for 24 hr. The solutions were made by dissolving the active agents of the invention in phosphate buffer, at pH 8 at a concentration of 100 mg/ml, which was then centrifuged at 25,000 rpm for 30 min at 25° C. in a Ti45 rotor. The supernatant solution was removed, and three 1 ml aliquots were dried down by centrifugation under an open vacuum for determining the concentration of the solution. The active agent is further diluted down to 2 mg/ml, filtered through a 0.2 $\mu$m acetate cellulose filter, and the concentration determined by determining the mass of the dried solute compared to the tared control.

The results demonstrated that Fraction 1 had an $ED_{50}$ range between 0.1 and 1.0 $\mu$g/ml and an $ED_{90}$ range between 0.2 and 2.5 $\mu$g/ml in preventing FIV infection of CrFK cells. Given these results, compositions of the invention may be administered in pharmaceutically acceptable carriers and should be administered in sufficient dosage to obtain a blood concentration of 10 nM to 1000 nM. However, in some instances it is necessary to administer doses to obtain concentration of up to 10,000 nM in the blood. The more active agents may be effective at blood concentration of as low 1 nM.

EXAMPLE 4

Conjugation of Salvianolic Acid

Under alkaline conditions, salvianolic acid (Compound 1) may generate three additional dehydrogenated forms (Compounds 2–4). The conjugation of salvianolic acid and its derivatives (dehydrogenated forms of salvianolic acid) to dimeric forms results in the formation of several compounds whose structures are shown. These conjugations are the result of homodimers and/or heterodimers of salvianolic acid with its dehydrogenated forms. These compounds show anti-HIV-1 integrase activity at concentrations less than 1 $\mu$g/ml.

The base structure of salvianolic acid, Compound 1, is shown (see below):

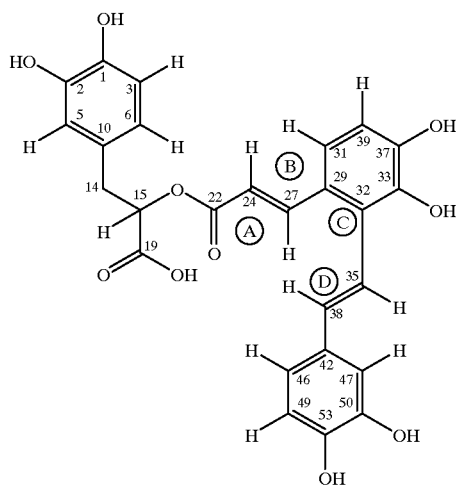

Figure 2:
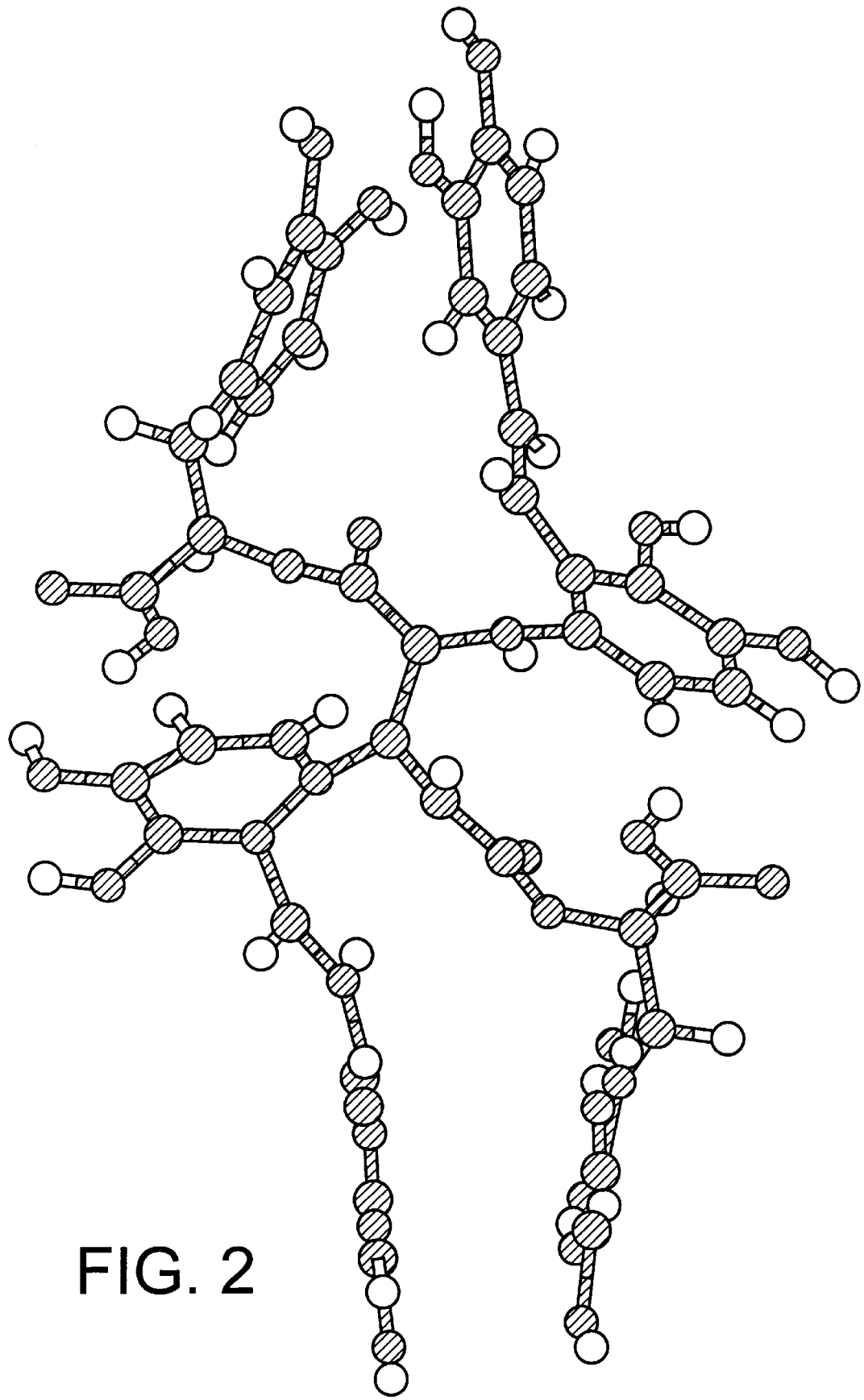
FIG. 2. Three-dimensional representation of Compound 6 of Example 4.
Figure 3:
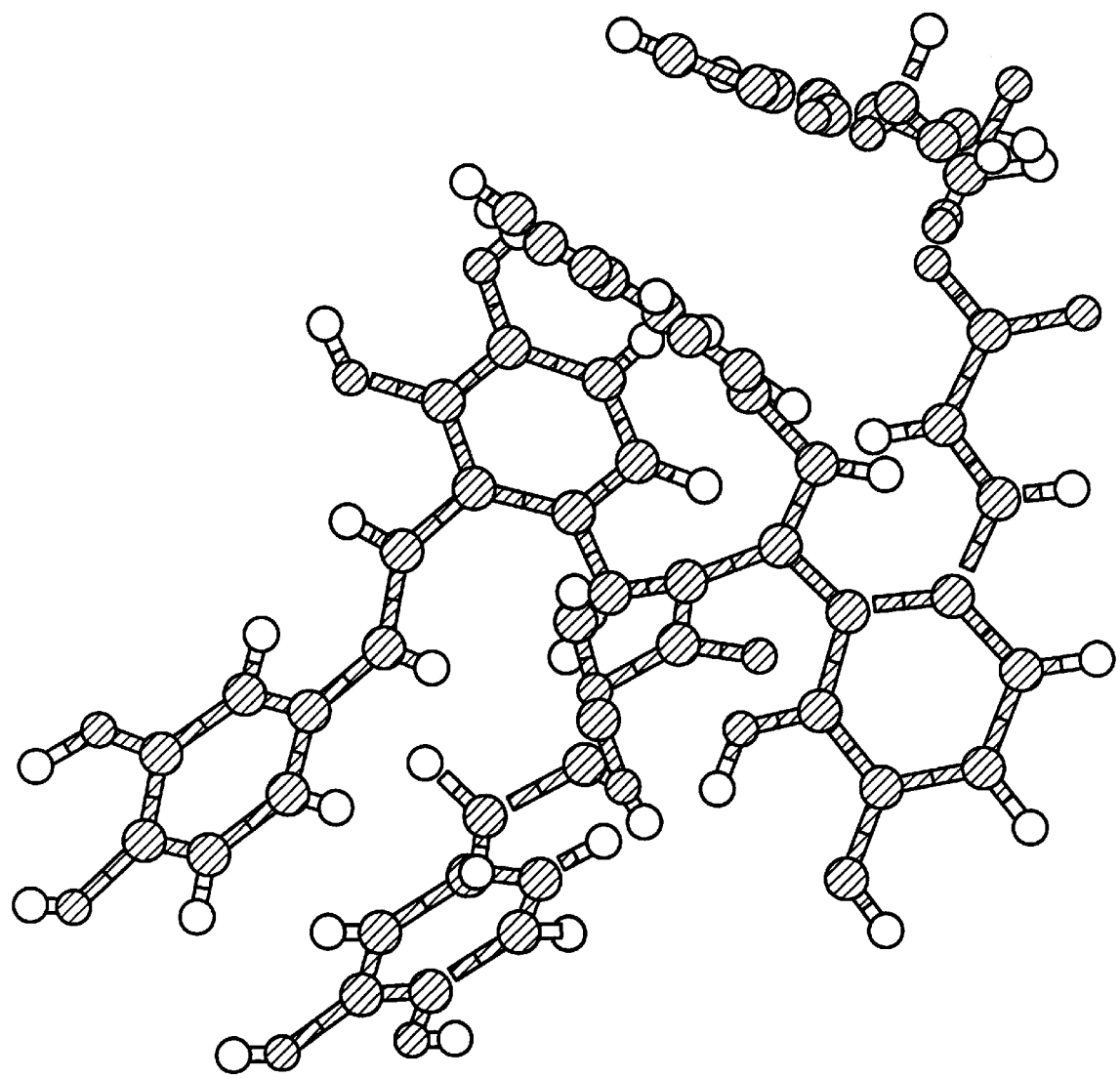
FIG. 3. Three-dimensional representation of Compound 7 of Example 4.
Figure 4:
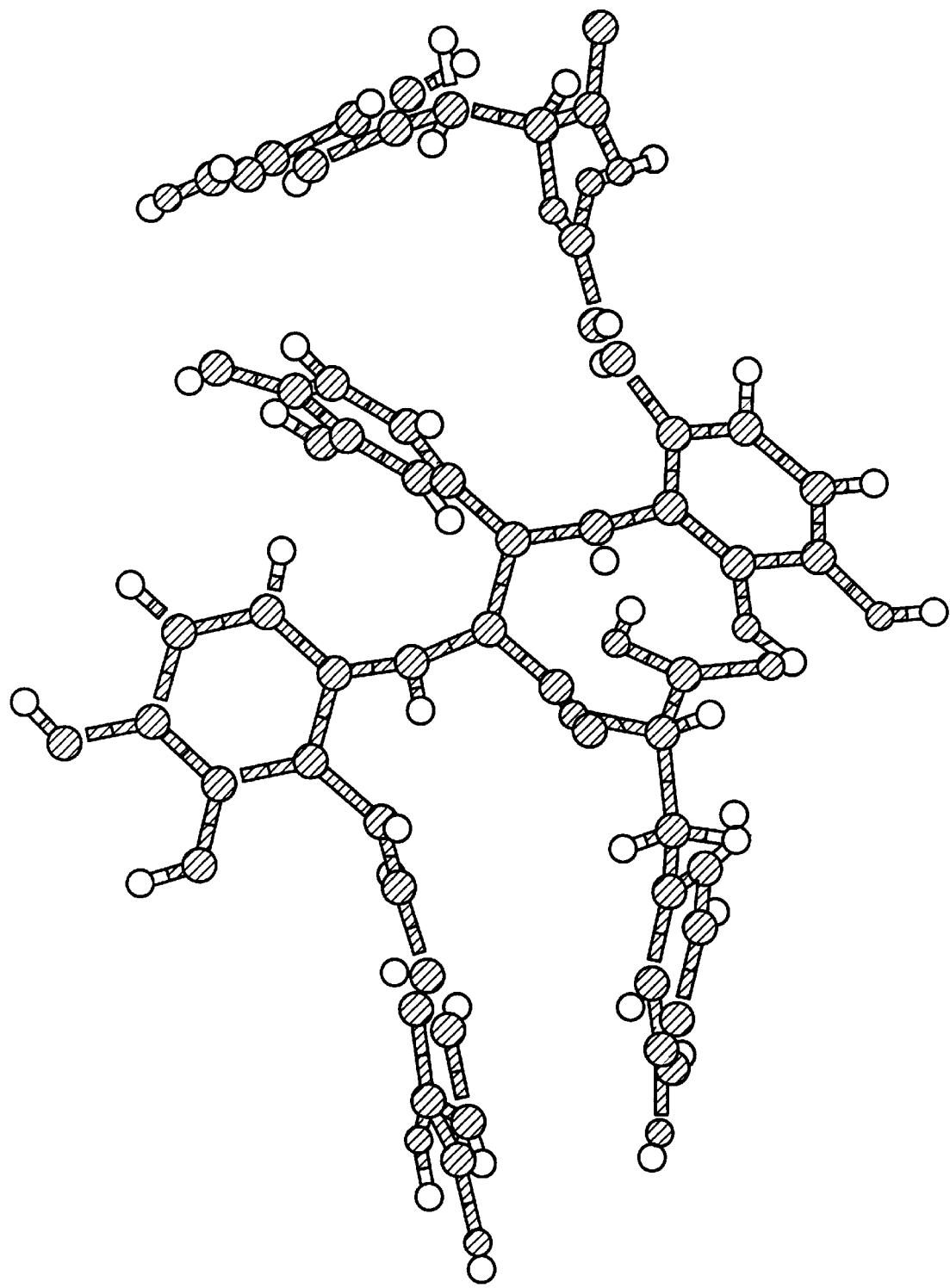
FIG. 4. Three-dimensional representation of Compound 8 of Example 4.
Figure 5:
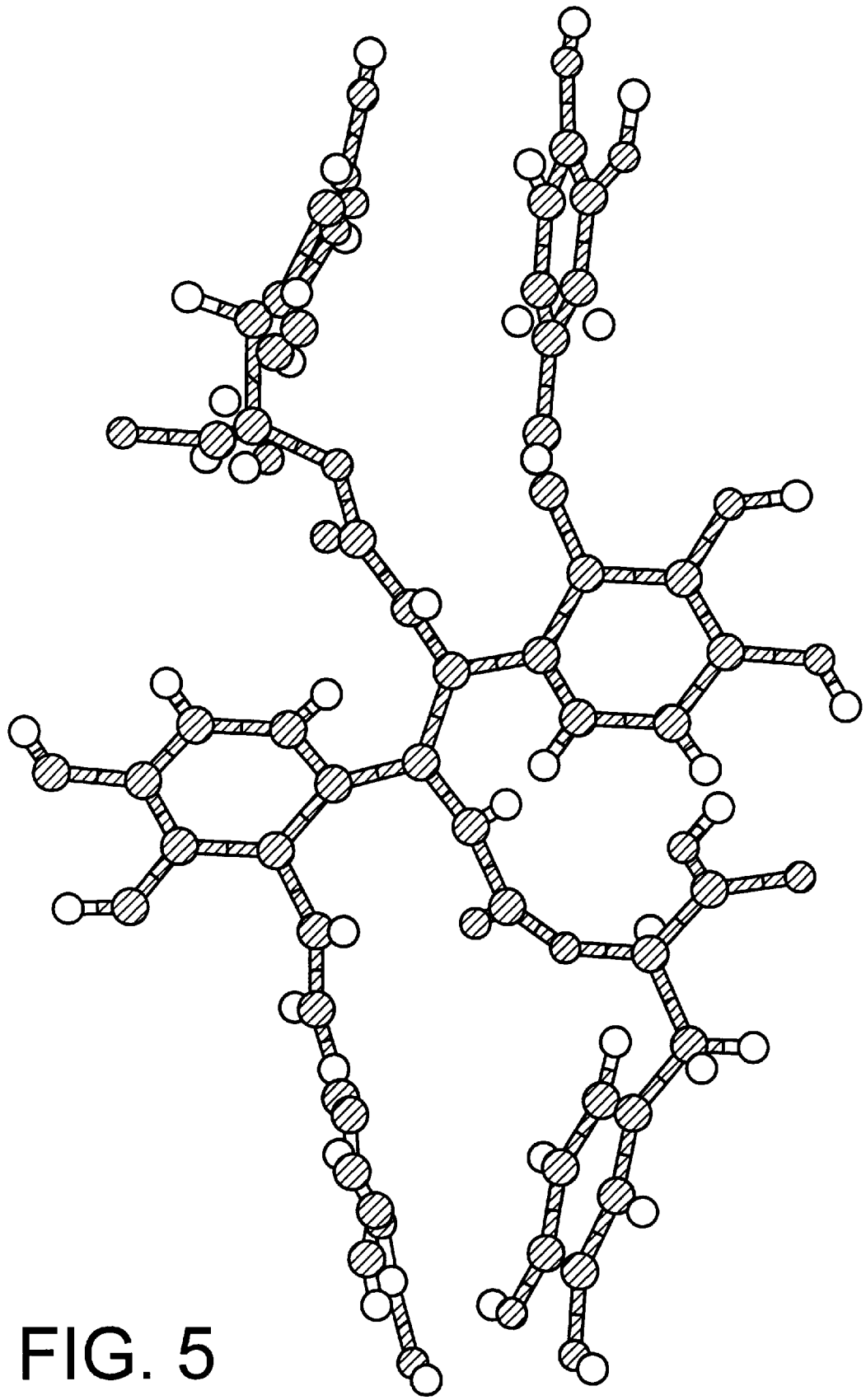
FIG. 5. Three-dimensional representation of Compound 9 of Example 4.
Figure 6:
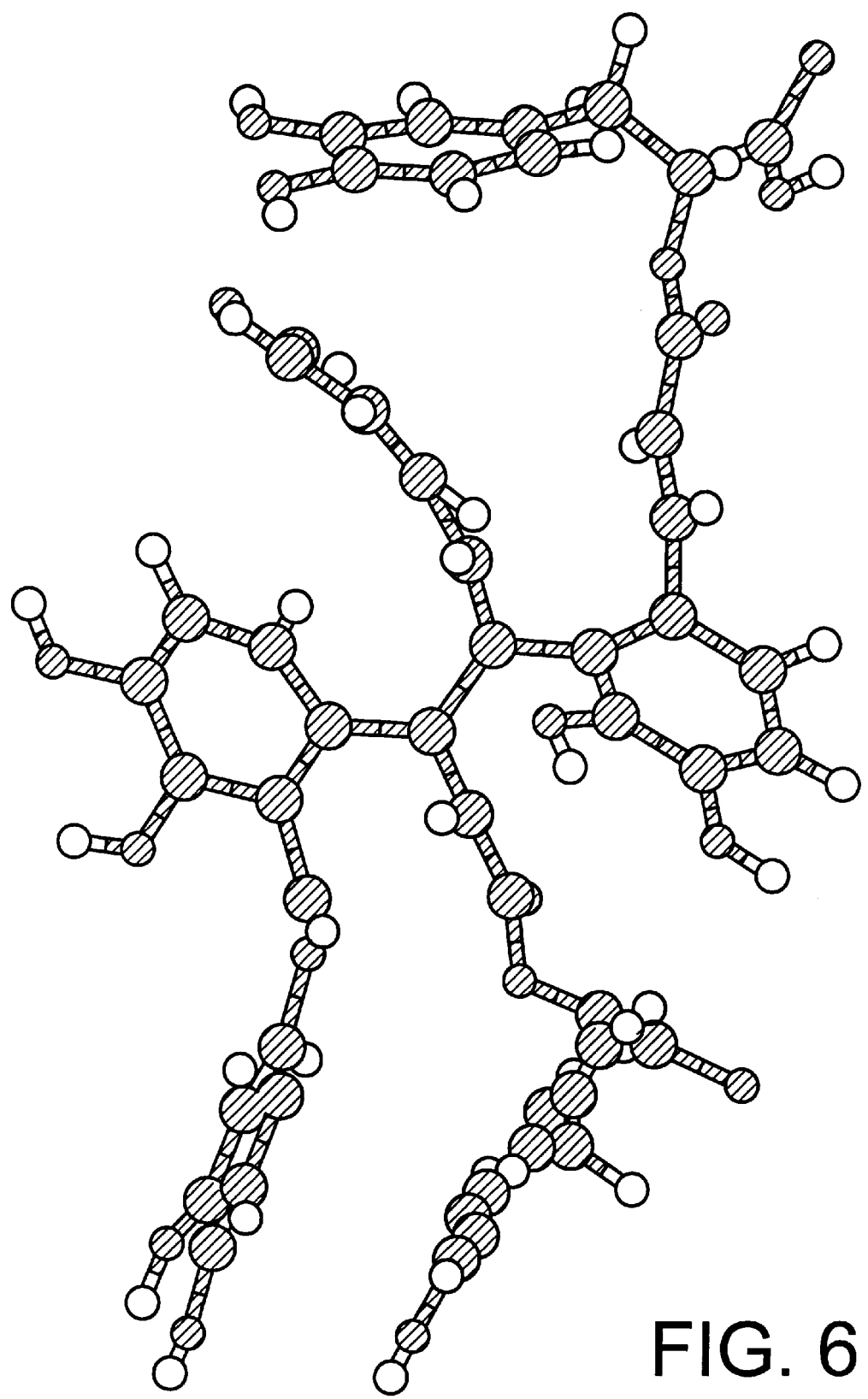
FIG. 6. Three-dimensional representation of Compound 10 of Example 4.
Figure 7:
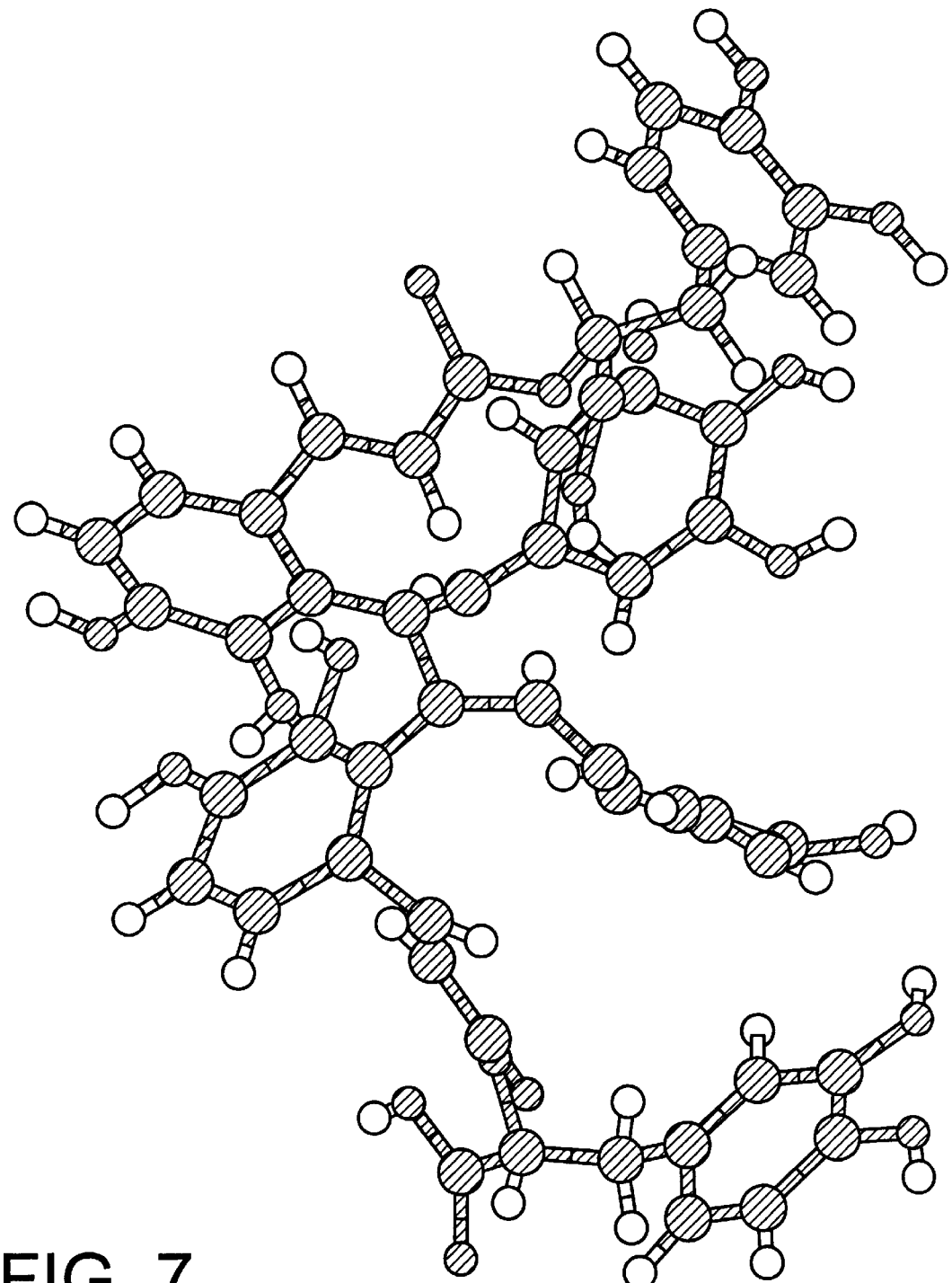
FIG. 7. Three-dimensional representation of Compound 11 of Example 4.
Figure 8:
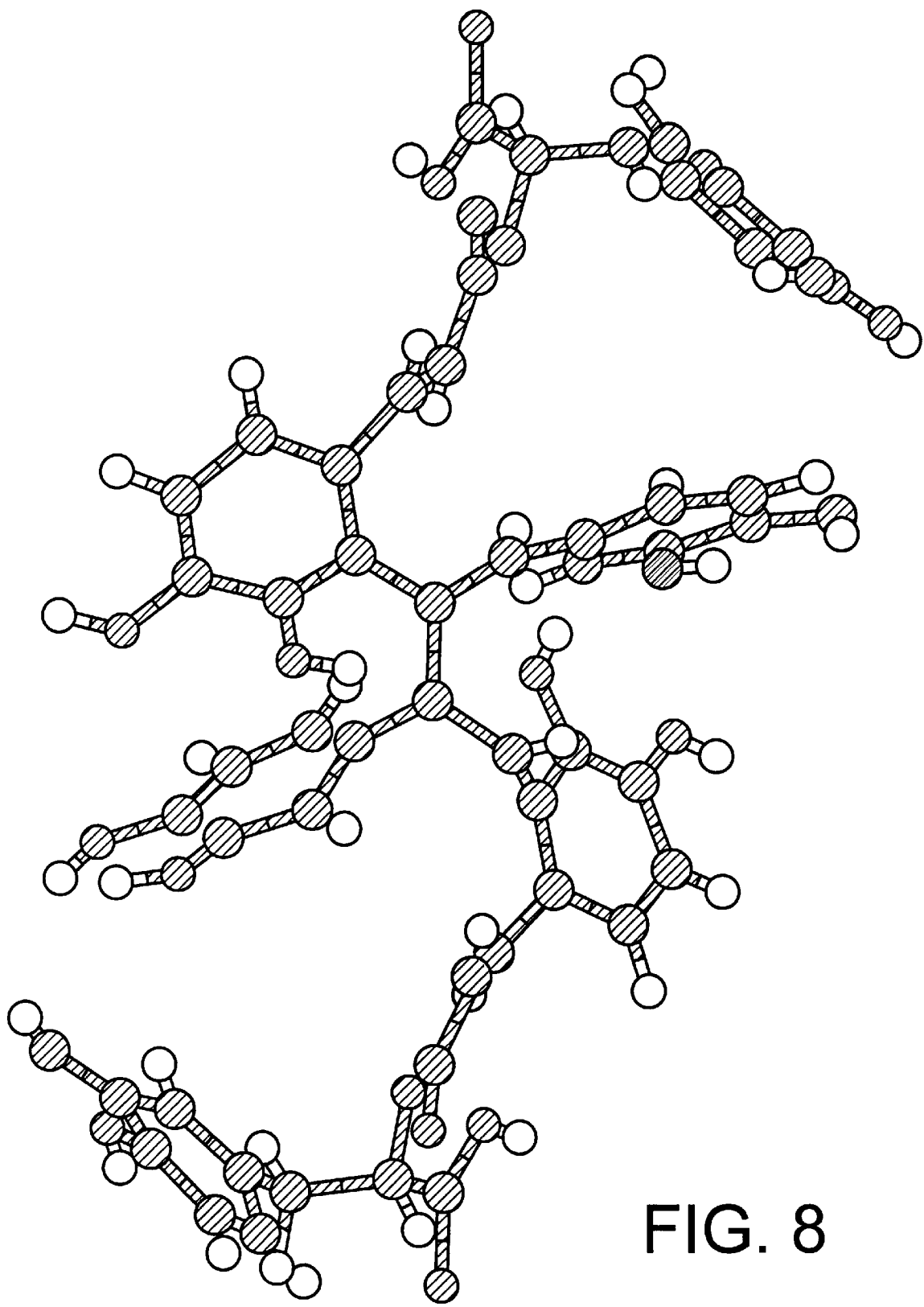
FIG. 8. Three-dimensional representation of Compound 12 of Example 4.
Figure 9:
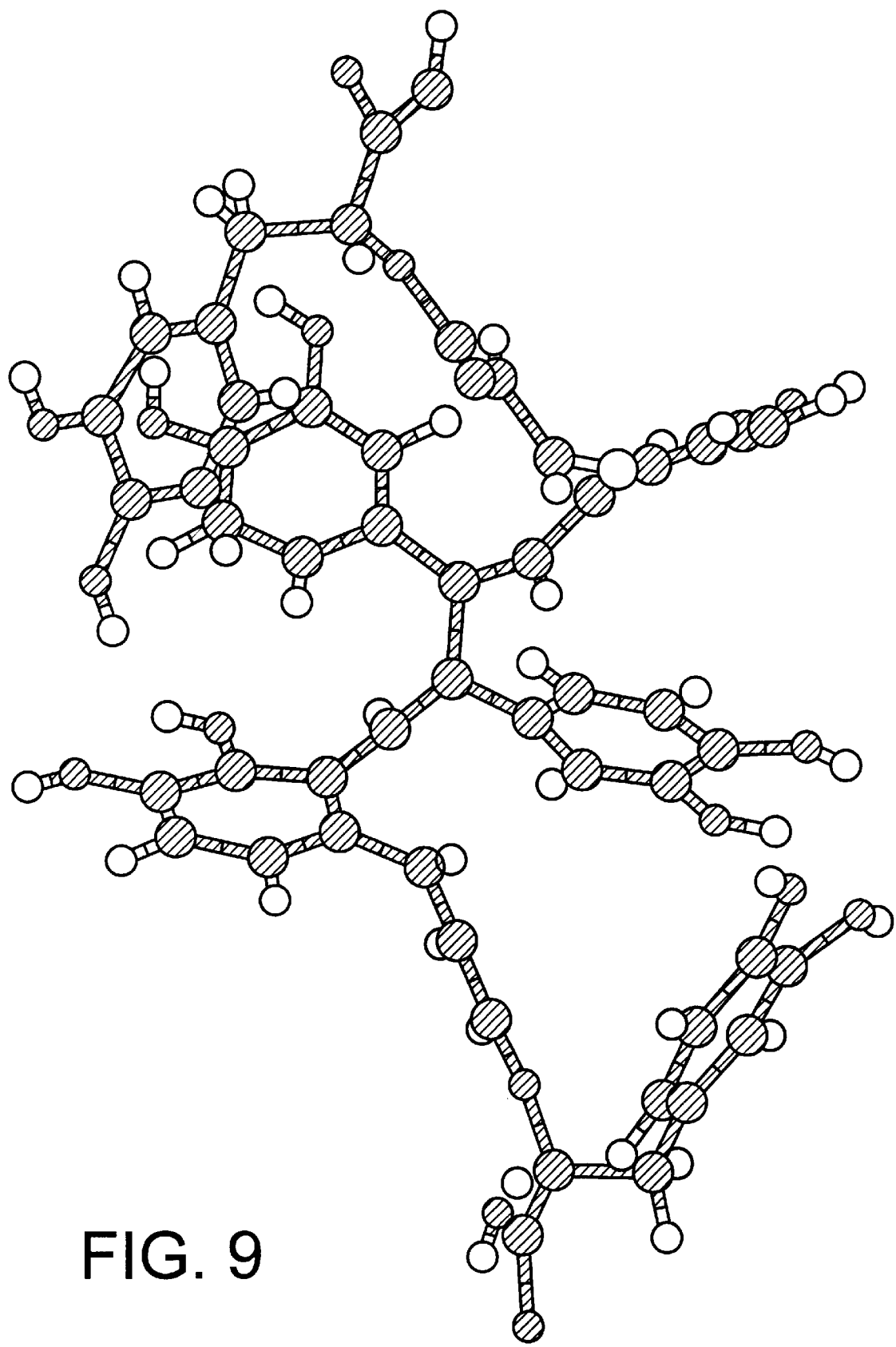
FIG. 9. Three-dimensional representation of Compound 13 of Example 4.
Figure 13:
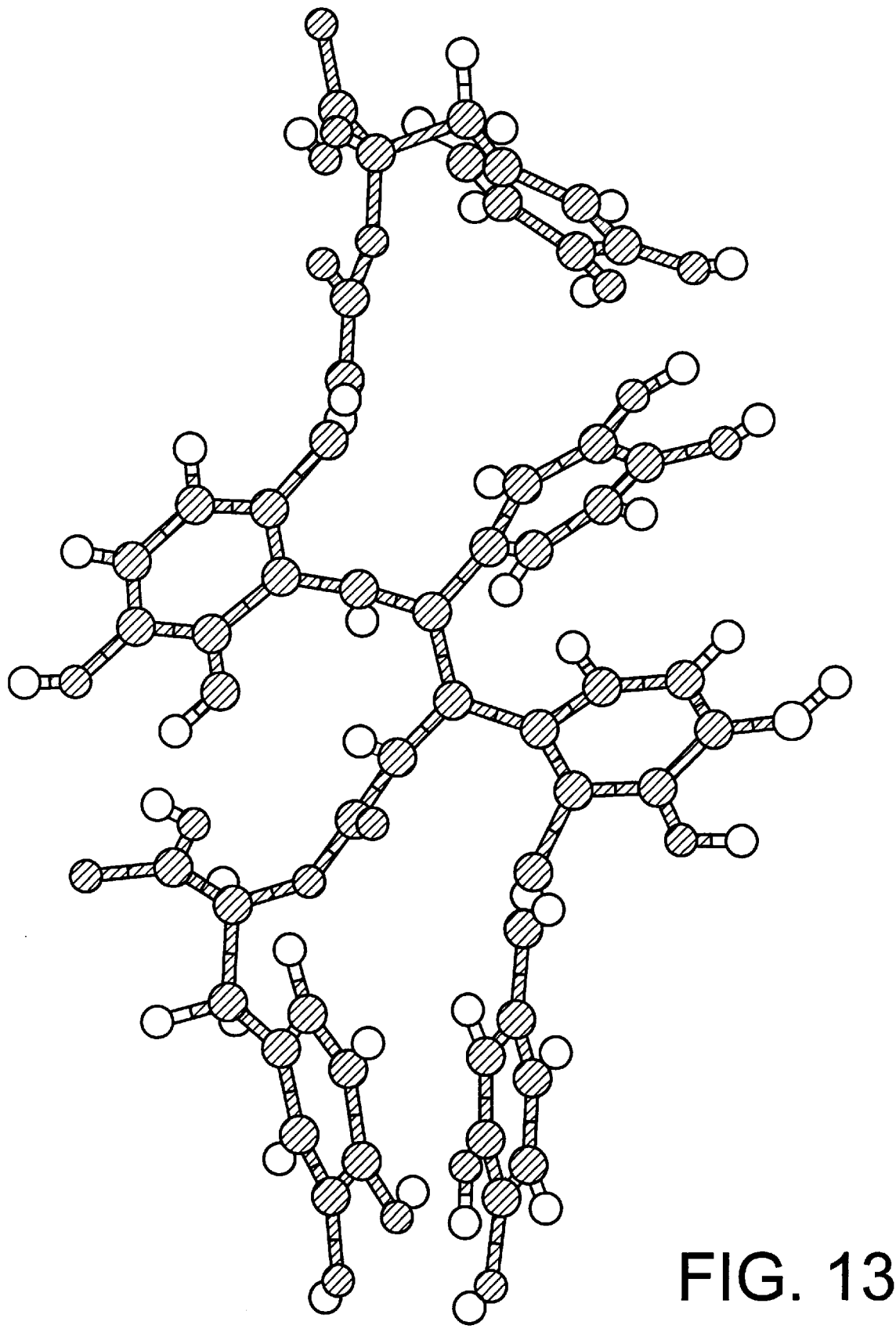
FIG. 13. Three-dimensional representation of Compound 24 of Example 4.

A, B, C, and D represent the hydrogens at carbons 24, 27, 35, and 38, respectively, of Compound 1. These hydrogens are the potential sites of conjugation. Therefore, the conjugation of salvianolic acid to itself (Compound 1), a homodimer, will result in the formation of the following combinations (Compounds 5–13): Compound 5 is A conjugated to A (FIG. 1); Compound 6 is A conjugated to B (FIG. 2); Compound 7 is A conjugated to C (FIG. 3); Compound 8 is A conjugated to D (FIG. 4); Compound 9 is B conjugated to B (FIG. 5); Compound 10 is B conjugated to C (FIG. 6); Compound 11 is C conjugated to C (FIG. 7); Compound 12 is C conjugated to D (FIG. 8); Compound 13 is D conjugated to D (FIG. 9); Compound 24 is B of Compound 1 conjugated to D of Compound 1 (FIG. 13).

Figure 10:
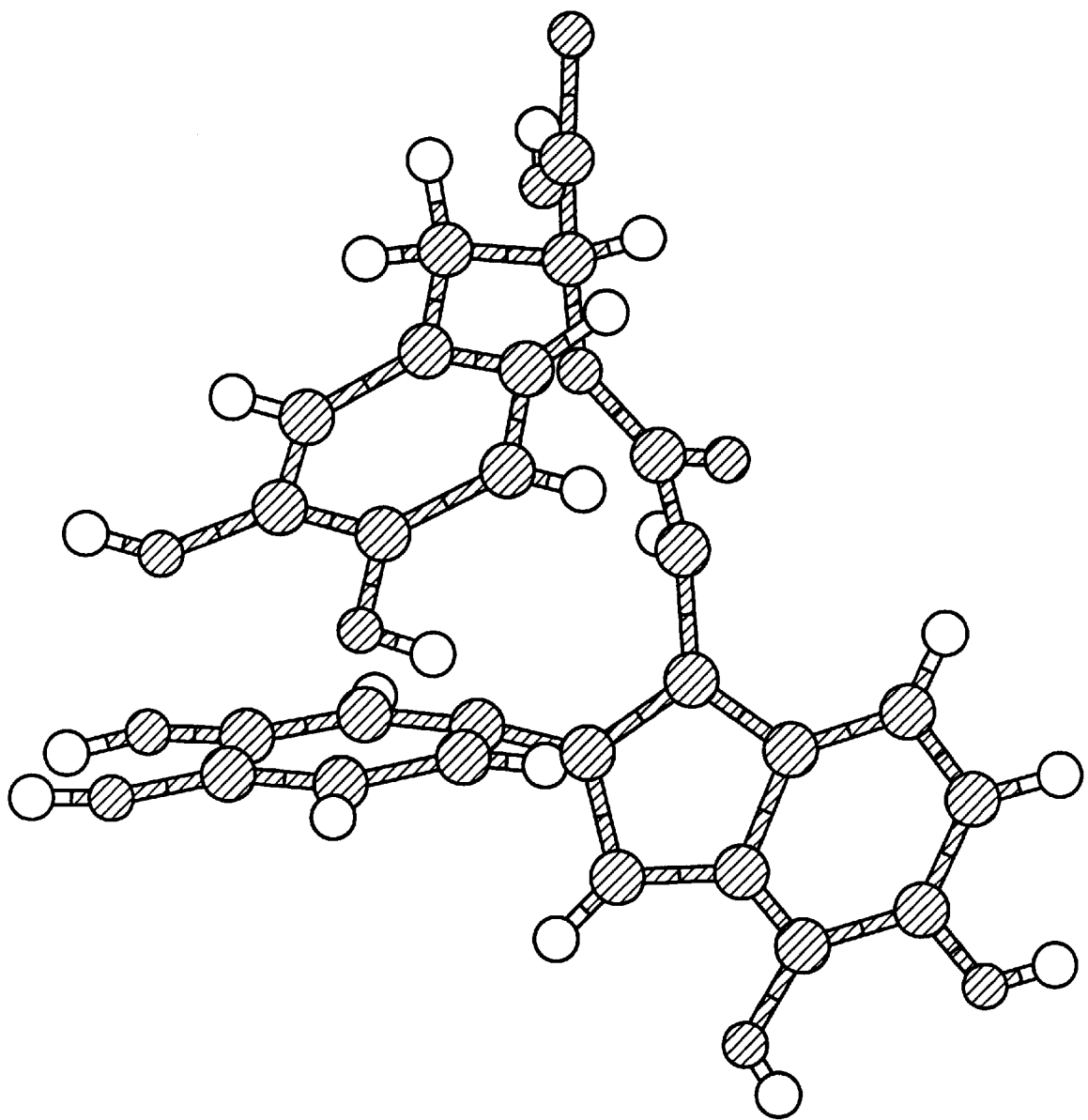
FIG. 10. Three-dimensional representation of Compound 2 of Example 4 formed by dehydrogenation of carbons 24 and 38 of salvianolic acid.

The three dehydrogenated forms of salvianolic acid (Compounds 2–4) that can be formed by dehydrogenation at carbons 24 and 38, carbons 24 and 35, and carbons 27 and 38. These forms have the following base structures:

Compound 2, 24–38 (FIG. 10):

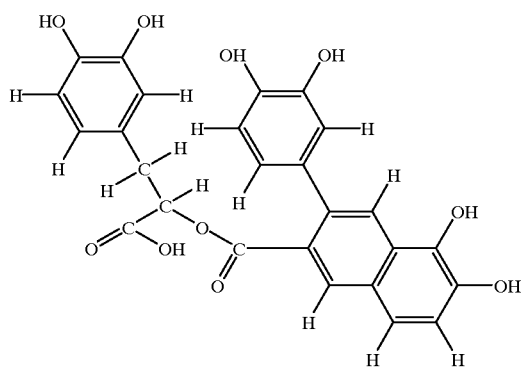

Figure 11:
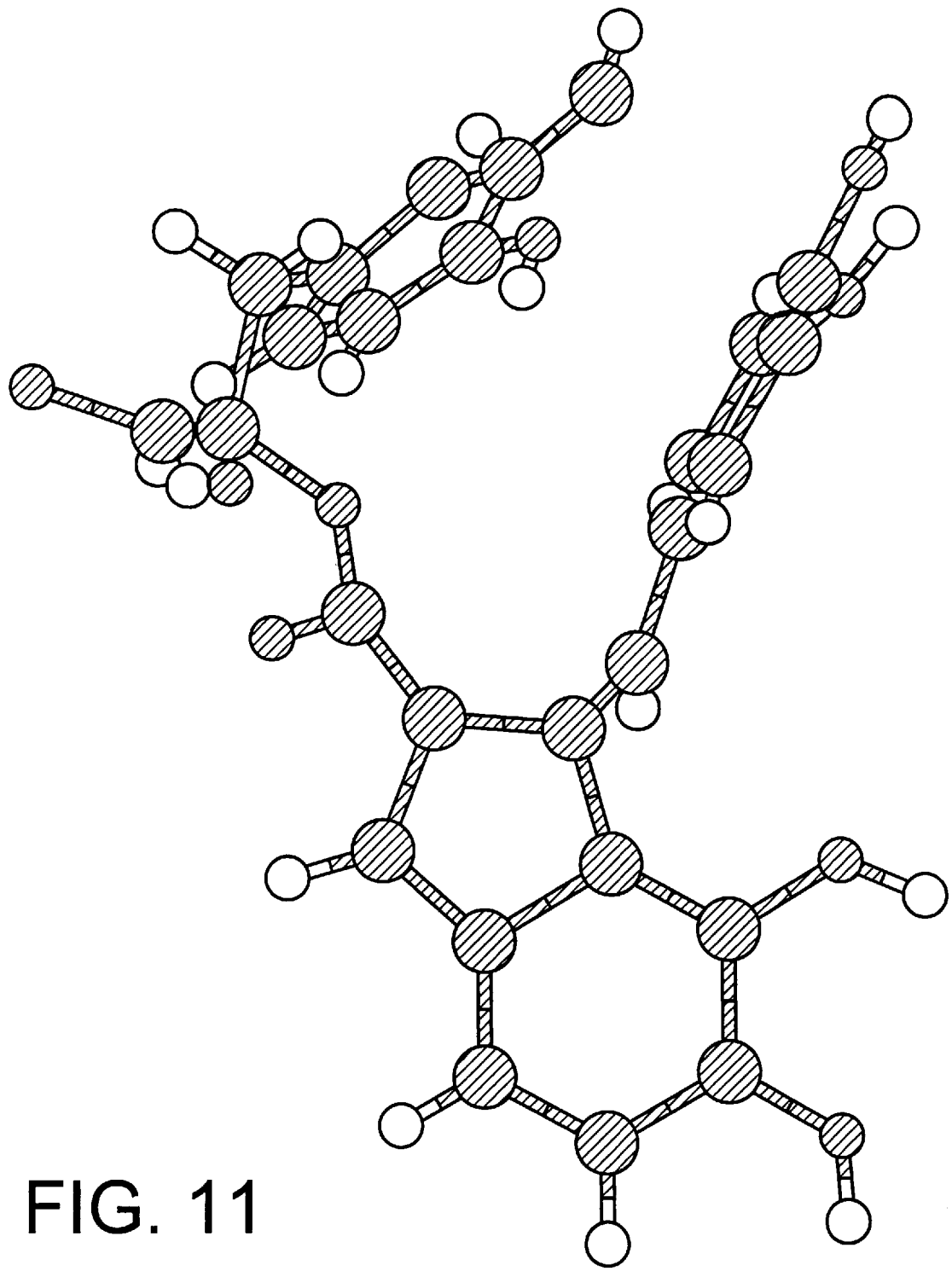
FIG. 11. Three-dimensional representation of Compound 3 of Example 4 formed by dehydrogenation of carbons 24 and 35 of salvianolic acid.

Compound 3, 24–35 (FIG. 11):

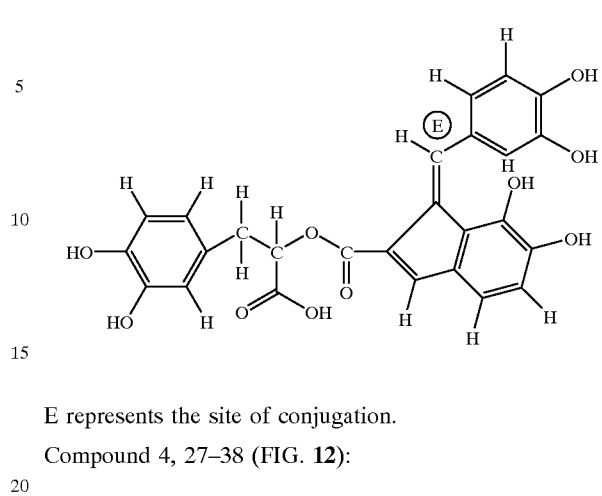

E represents the site of conjugation.

Figure 12:
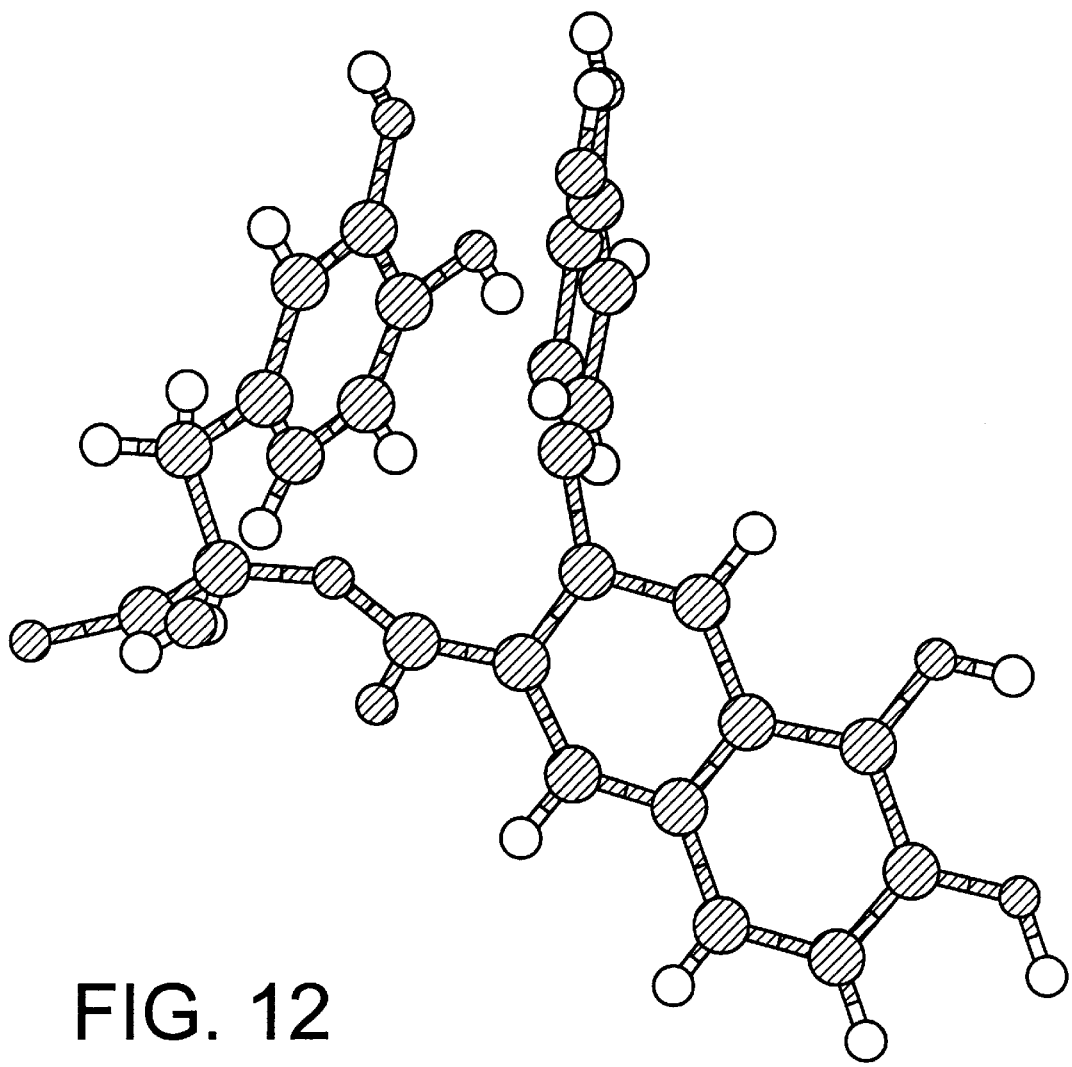
FIG. 12. Three-dimensional representation of Compound 4 of Example 4 formed by dehydrogenation of carbons 27 and 38 of salvianolic acid.

Compound 4, 27–38 (FIG. 12):

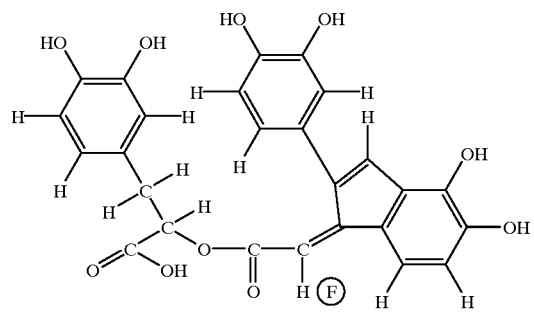

F represents the site of conjugation.

The dehydrogenated forms of salvianolic acid (Compounds 2–4) can form homodimers. This means that compound 3 can conjugate with itself at site E to form Compound 14, and Compound 4 conjugates with itself at site F to form Compound 15.

These dehydrogenated forms can also form heterodimers with salvianolic acid. The potential heterodimers that are formed are A of Compound 1 conjugated with E of Compound 3 to form Compound 16; B of Compound 1 conjugated with E of Compound 3 to form Compound 17; C of Compound 1 conjugated with E of Compound 3 to form Compound 18; D of Compound 1 conjugated with E of Compound 3 to form Compound 19; F of Compound 4 conjugated with A of Compound 1 to form Compound 20; F of Compound 4 conjugated with B of Compound 1 to form Compound 21; F of Compound 4 conjugated with C of Compound 1 to form Compound 22; and F of Compound 4 conjugated with D of Compound 1 to form Compound 23.

In addition to these dimers, it is possible to form trimers and larger polymers of these species. The variations in structure of these compounds will be known to those skilled in the art.

It is also envisioned that these compounds can be modified to contain acetyl groups, esters, anhydrides or pharmaceutically acceptable salts of the compound.

EXAMPLE 5

Time Dependent Activation of Anti-integrase Activity as a Result of Conjugation Compound 1 of Example 4 was purified and confirmed by both Mass Spectrometry and NMR. Compound 1 was then incubated with 0.1% $NH_4OH$ for various time periods (5 min., 30 min., 1 hr., 2 hrs., 3 hrs., 4 hrs., 5 hrs. and 24 hrs.) at a concentration of 5 mg/ml. The reactions were stopped by the addition of 1% acetic acid and assayed for anti-HIV-1 integrase activity. The results demonstrate that there is a time-dependent activation of the fractions as a result of incubation in 0.1% $NH_4OH$. This activation is the result of various conjugations of Compound 1. The results are displayed in Table 3:

TABLE 3

| Time pH 6.0 | $IC_{50}$ (µg/ml) |
|---|---|
| pH = 6.0 | 3.5 |
| 5 min. | 1.8 |
| 30 min. | 1.7 |
| 1 hr. | 1.5 |
| 2 hrs. | 1.5 |
| 3 hrs. | 1.05 |
| 4 hrs. | 1.0 |
| 5 hrs. | 0.9 |
| 24 hrs. | 0.5 |

Purified compounds having a MW of 492 (e.g., compounds 2–4, as described above) were incubated with 0.1% $NH_4OH$ for various time periods (5 min., 30 min., 1 hr., 1.5 hr., 2.0 hrs., and 3.0 hrs.) at a concentration of 5.0 mg/ml. The reactions were stopped by the addition of 1% acetic acid and assayed for anti-HIV-1 integrase activity. The results demonstrate that there is a time-dependent activation of Compounds 2–4 as a result of incubation in 0.1% $NH_4OH$. This activation, however, is not as great as conjugations with Compound 1. The results are shown in Table 4:

TABLE 4

| Sample | IC 50 |
|---|---|
| 5 min. | >7.5 |
| 30 min. | 5.5 |
| 1 hr. | 5.2 |
| 1.5 hrs. | 4.2 |
| 2.0 hrs. | 4.1 |
| 3.0 hrs | 2.1 |

EXAMPLE 6

Anti-HIV-1 Integrase Activity of Activated Compound 1

0.8 g of Compound 1 of Example 4 was incubated in 80 ml of 0.1% $NH_4OH$ to a final concentration of 10 mg/ml for 8 hrs. This activated fraction was then applied to an SEPHADEX® TH20 column and eluted with increasing concentrations of methanol in water. The eluted fractions were lyophilized and assayed for anti-HIV-1 integrase activity. The results are shown in Table 5:

TABLE 5

| Fraction | $IC_{50}$ (λg/ml) |
|---|---|
| Original | 1.1 |
| 10% Methanol | 1.1 |
| 20% Methanol | 0.69 |
| 30% Methanol | 0.81 |
| 40% Methanol | 0.92 |
| 50% Methanol | 0.4 |
| 60% Methanol | 0.92 |
| 70% Methanol | 3.2 |
| 80% Methanol | >7.5 |

The 50% sample, which had the best activity, was then analyzed by mass spectrometry. The mass spectra showed two major peaks of 492 and 986. These peaks correspond to a monomer of salvianolic acid and a dimer of salvianolic acid, indicating that these species represent the active antiviral principles. Therefore, these results suggest that the active anti-viral agent responsible for the inhibition of integrase is either salvianolic acid and/or its dimeric form.

The efficacy of these fractions against HIV-1 infection was evaluated using $CEM^{TART}$ cells. These cells are engineered from CEM as described in Example 8. The HIV p24 antigen capture assay was used as described in Example 8. The results are discussed in Table 6 below:

TABLE 6

| Sample | IC 50 (µg/ml) |
|---|---|
| 10% | 41 |
| 20% | 2.2 |
| 30% | 12 |
| 40% | 7 |
| 50% | 3.8 |
| 60% | 40 |
| 70% | 40 |
| 80% | Not Determined |

EXAMPLE 7

Anti-HIV-1 Integrase Activity

Fraction 1 of Example 1 was dissolved in 40% of methanol (in water) and centrifuged for 30 min. at 8,000 rpm in a GSA rotor. The supernatant fraction was loaded onto a SEPHADEX® LH20 column equilibrated in 40% methanol (in water). The column was washed with 40% methanol solution (in water) and eluted with 50, 60, 70, 80 and 90% of methanol solution (in water). The samples were then lyophilized and dissolved in the appropriate volume of methanol to make the final stock concentration 5 mg/ml. These fractions were then assayed for anti-HIV-1 integrase activity. The concentrations assayed were 5, 2.5, 2, 1.5, 1.25, 1, 0.8, 0.6, 0.4, and 0.2 µg/ml. The percent of inhibition was determined by subtracting the percent of cleavage of each fraction from the percent of cleavage of the positive control and dividing this value by the percent of cleavage of the positive control.

TABLE 7

Results of In vitro HIV-1 Integrase Activity Assay

| # Fractions | IC$_{50}$ (μg/ml) |
|---|---|
| 40 | 0.84 |
| 50 | 0.70 |
| 60 | 0.68 |
| 70 | 0.60 |
| 80 | 0.57 |
| 90 | 0.50 |

SEPHADEX® LH20 column fractions of 60–80% were combined and dissolved in 40% of methanol in water. The resuspended sample was centrifuged for 30 min at 8,000 rpm in a GSA rotor. The supernatant solution was applied to MCI GEL CHP20P (75–150 μ) column equilibrated with 40% methanol in water. The column was washed with 40% methanol in water and eluted with 50, 60, and 70% of methanol in water. The sample was then lyophilized and assayed as previously described under various conditions.

TABLE 8

Results of In vitro HIV-1 Integrase Activity Assay

| # samples | IC$_{50}$ in MeOH (μg/ml) | IC$_{50}$ in pH 6.0 (μg/ml) | IC$_{50}$ in 0.1% NH$_4$OH λg/ml) |
|---|---|---|---|
| MCI 40 | 0.32 | 0.70 | 0.44 |
| MCI 50 | 0.34 | 0.80 | 0.58 |
| MCI 60 | 0.42 | 1.00 | 0.62 |

The MCI GEL CHP20P (75–150 μ) samples were then analyzed by Mass Spectrometry Analysis (negative mode). The results show that MCI 40 has a major peak of 986 with a minor peak of 494. The MCI 50 has major peaks of 492 and 986. MCI 60 has major peaks of 984 and 986. It was determined that the 494 peak represents salvianolic acid as determined by Mass Spectrometry and NMR. The 492 peak represents the dehydrogenated form of salvianolic acid. The 986 peak represents a dimeric form of salvianolic acid. The 984 peak represents the mixed dimer of 492 and 494. These results indicate that the active principles of Fraction 1 are a Compound having a molecular weight of 984 and/or 986. These experimental data suggest that the dimeric compounds of molecular weight 984 and 986 are generated from Compound 1.

EXAMPLE 8

Assaying the Anti-HIV-1 Activity of an Active Agent

The efficacy of the MCI GEL CHP20P (75–150 μ) fractions against HIV-1 infection was evaluated with CEM$^{TART}$ cells. These cells are engineered from CEM cells and consitutively express HIV-1 tat and rev genes. CEM$^{TART}$ cells provide a safe system for assessing HIV infection as they have been engineered to be productive for a replication incompetent form of the HIV-1, HIV$^{\Delta tat/rev}$. The efficacy of the compounds to inhibit HIV-1 infection was evaluated using the HIV p24 antigen capture assay. This assay uses p24 core protein monoclonal antibody coated 96 well plates in which cell culture media or serum was incubated for 2 hrs. The supernatants were removed from cells at least 1 week following infection with HIV$^{\Delta tat/rev}$. The wells were washed prior to the addition of a biotinylated polyclonal antibody to HIV-1 p24. Following addition of substrate for signal amplification, p24 expression is directly quantified relative to the known standard.

MCI 40, 50 and 60 were dissolved in methanol, and the ability of these compounds to inhibit HIV-1 infection was assessed at the following concentrations: 100, 20, 10, 5, and 1 μg/ml. To 24 well tissue culture dishes, 2 ml of 3.33×10$^4$ CEM$^{TART}$ cells were added together with the test concentrations of compound. To this 5000 TCID$_{50}$/10$^6$ cells of HIV-1 inoculum was added. The culture medium was changed twice weekly such that 0.8 ml of cell suspension was resuspended in 2 ml of replacement medium. Cell-free supernatants were then assayed for the presence of p24. Anti-HIV-1 efficacy was then evaluated by comparing HIV-1 p24 antigen production in the presence and absence of added drug after 7 and 10 days. The results are shown in Tables 9 and 10:

TABLE 9

Day 7

| Sample | Concentration (μg/ml) | % Inhibition |
|---|---|---|
| MCI 40 | 100 | 100 |
| | 20 | 100 |
| | 10 | 100 |
| | 1 | 0 |
| MCI 50 | 100 | 100 |
| | 20 | 100 |
| | 10 | 100 |
| | 1 | 0 |
| MCI 60 | 100 | 100 |
| | 20 | 100 |
| | 10 | 100 |
| | 1 | 0 |

TABLE 10

Day 10

| Sample | Concentration (μg/ml) | % Inhibition |
|---|---|---|
| MCI 40 | 100 | 100 |
| | 20 | 100 |
| | 10 | 100 |
| | 1 | 0 |
| MCI 50 | 100 | 100 |
| | 20 | 100 |
| | 10 | 100 |
| | 1 | 0 |
| MCI 60 | 100 | 100 |
| | 20 | 100 |
| | 10 | 100 |
| | 1 | 0 |

All references discussed above are hereby incorporated by reference. Also incorporated by reference is parent application, U.S. application Ser. No. 09/104,363 filed Jun. 25, 1998.

What we claim is:

1. A conjugation product which is a homopolymer or heteropolymer of monomeric units of salvianolic acid and/or dehydrogenated forms of salvianolic acid, said conjugation product having a molecular weight of about 492 or greater, or acetyl, ester, or anhydride derivatives thereof, or pharmaceutically acceptable salts thereof.

2. The conjugation product according to claim 1, which has a molecular weight ranging from about 492 to about 986.

3. The conjugation product according to claim 2, which has a molecular weight of about 492.

4. The conjugation product according to claim 2, which has a molecular weight of about 984.

5. The conjugation product according to claim 2, which has a molecular weight of about 986.

6. The conjugation product according to claim 1, which is a homopolymer or heteropolymer of monomeric units of salvianolic acid and/or dehydrogenated forms II or III of salvianolic acid, said salvianolic acid having the structure:

(I)

and said dehydrogenated forms of salvianolic acid having the structures:

(II)

(III)

wherein $R^1$, $R^2$, $R^3$, $R^4$, $R^5$, and $R^6$ are hydrogen or a bond, and the monomeric units of said homopolymers or heteropolymers are bonded to each other by $R^1$, $R^2$, $R^3$, $R^4$, $R^5$, and/or $R^6$.

7. The conjugation product of claim 6 which is a homodimer.

8. The conjugation product of claim 7, wherein the monomeric units are bonded together by a bond which is $R^1$—$R^1$, $R^2$—$R^2$, $R^3$—$R^3$, $R^4$—$R^4$, $R^5$—$R^5$, or $R^6$—$R^6$.

9. The conjugation product of claim 7, wherein the monomeric units are bonded together by a bond which is $R^1$—$R^2$, $R^1$—$R^3$, $R^1$—$R^4$, $R^2$—$R^3$, $R^2$—$R^4$, or $R^3$—$R^4$.

10. The conjugation product of claim 6 which is a heterodimers.

11. The conjugation product of claim 10, wherein the monomeric units are bonded together by a bond which is $R^1$—$R^5$, $R^2$—$R^5$, $R^3$—$R^5$, or $R^4$—$R^5$.

12. The conjugation product of claim 10, wherein the monomeric units are bonded together by a bond which is $R^1$—$R^6$, $R^2$—$R^6$, $R^3$—$R^6$, $R^4$—$R^6$, or $R^5$—$R^6$.

13. The conjugation product of claim 1 which is a homotrimer.

14. The conjugation product of claim 1 which is a heterotrimer.

15. The conjugation product of claim 1 which is a homopolymer of 4 or more monomeric units.

16. The conjugation product of claim 1 which is a heteropolymer of 4 or more monomeric units.

17. A method of treating a patient having or at risk to have a viral infection by administering thereto a composition containing a viral-inhibiting effective amount of a conjugation product according to claim 1.

18. The method according to claim 17, wherein the conjugation product is a homodimer, heterodimer, homotrimer or heterotrimer.

19. The method according to claim 17, wherein the viral infection is caused by a hepatitis virus, orthomyxovirus, papillomavirus, paramyxovirus, picornavirus, polyomavirus or retrovirus.

20. The method according to claim 19, wherein the retrovirus is HIV or FIV.

21. The method according to claim 19, wherein the viral infection is caused by a virus that produces integrase or a protein which has integrase activity.

22. The method according to claim 17, wherein the conjugation product is administered intranasally, orally, transdermally, parenterally, intrathecally or intravenously.

23. A method of making an antiviral agent comprising incubating salvianolic acid at an alkaline pH such that homopolymers or heteropolymers are formed which possess greater antiviral activity than salvianolic acid.

24. The method according to claim 23, wherein the homopolymers or heteropolymers have a molecular weight of about 492 or greater.

25. The method according to claim 23, wherein the homopolymers or heteropolymers have a molecular weight ranging from about 492 to about 986.

26. The method according to claim 25, wherein the homopolymers or heteropolymers have a molecular weight of about 492.

27. The method according to claim 25, wherein the homopolymers or heteropolymers have a molecular weight of about 984.

28. The method according to claim 25, wherein the homopolymers or heteropolymers have a molecular weight of about 986.

29. The method according to claim 23, wherein the homopolymers or heteropolymers comprise monomeric units of salvianolic acid and/or dehydrogenated forms II or III of salvianolic acid, said salvianolic acid having the structure:

(I)

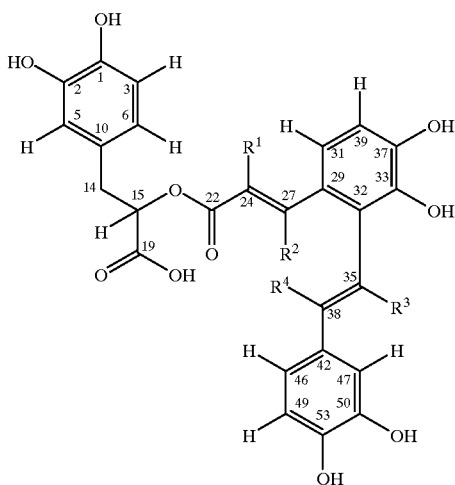

and said dehydrogenated forms of salvianolic acid having the structures:

(II)

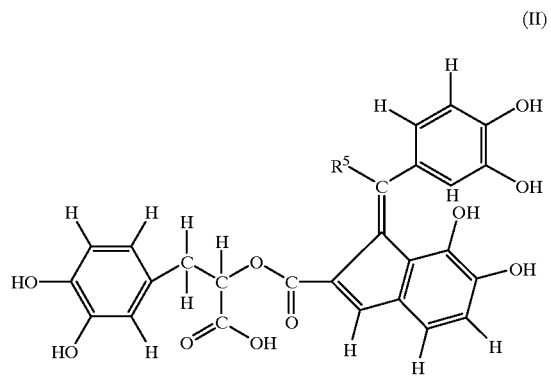

-continued (III)

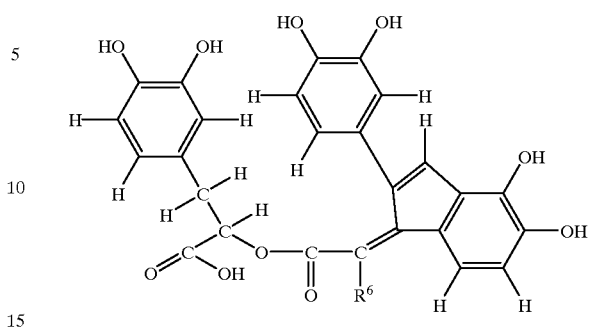

wherein $R^1$, $R^2$, $R^3$, $R^4$, $R^5$, and $R^6$ are hydrogen or a bond, and the monomeric units of said homopolymers or heteropolymers are bonded to each other by $R^1$, $R^2$, $R^3$, $R^4$, $R^5$, and/or $R^6$.

30. The method according to claim 29, wherein a homodimer is formed.

31. The method according to claim 30, wherein the monomeric units are bonded together by a bond which is $R^1$—$R^1$, $R^2$—$R^2$, $R^3$—$R^3$, $R^4$—$R^4$, $R^5$—$R^5$, or $R^6$—$R^6$.

32. The method according to claim 36, wherein the monomeric units are bonded together by a bond which is $R^1$—$R^2$, $R^1$—$R^3$, $R^1$—$R^4$, $R^2$—$R^3$, $R^2$—$R^4$, or $R^3$—$R^4$.

33. The method according to claim 29, wherein a heterodimers is formed.

34. The method according to claim 33, wherein the monomeric units are bonded together by a bond which is $R^1$—$R^5$, $R^2$—$R^5$, $R^3$—$R^5$, or $R^4$—$R^5$.

35. The method according to claim 33, wherein the monomeric units are bonded together by a bond which is $R^1$—$R^6$, $R^2$—$R^6$, $R^3$—$R^6$, $R^4$—$R^6$, or $R^5$—$R^6$.

36. The method according to claim 23, wherein a homotrimer is formed.

37. The method according to claim 23, wherein a heterotrimer is formed.

38. The method according to claim 23, wherein a homopolymer of 4 or more monomeric units is formed.

39. The method according to claim 23, wherein a heteropolymer of 4 or more monomeric units is formed.

* * * * *